United States Patent [19]

Welch et al.

[11] Patent Number: 5,037,743

[45] Date of Patent: Aug. 6, 1991

[54] BAR1 SECRETION SIGNAL

[75] Inventors: Susan K. Welch, Los Altos Hills, Calif.; Vivian L. MacKay, Seattle; Carli L. Yip, Bellevue, both of Wash.

[73] Assignee: ZymoGenetics, Inc., Seattle, Wash.

[21] Appl. No.: 270,933

[22] Filed: Nov. 14, 1988

Related U.S. Application Data

[63] Continuation-in-part of Ser. No. 229,074, Aug. 5, 1988, abandoned, which is a continuation-in-part of Ser. No. 104,316, Oct. 2, 1987, abandoned.

[51] Int. Cl.$^5$ .................. C12N 1/16; C12N 5/06; C12N 15/11; C12N 15/79
[52] U.S. Cl. ................. 435/69.1; 435/240.2; 435/255; 435/172.3; 435/320.1; 536/27; 935/48; 935/60; 935/69; 935/70
[58] Field of Search ............. 435/68, 69.1; 935/320, 935/32, 48, 57, 70, 71, 28; 536/27, 240.2, 255, 172.3

[56] References Cited

U.S. PATENT DOCUMENTS

| 4,546,082 | 10/1985 | Kurjan et al. | 435/172.3 |
|---|---|---|---|
| 4,593,002 | 6/1986 | Dulbecco | 435/172.3 |
| 4,613,572 | 9/1986 | MacKay et al. | 435/253 |
| 4,711,844 | 12/1987 | Chang | 435/317.1 |
| 4,751,180 | 6/1988 | Cousens et al. | 435/68 |
| 4,801,542 | 1/1989 | Murray et al. | 435/172.3 |

FOREIGN PATENT DOCUMENTS

| 0121884 | 10/1984 | European Pat. Off. | 935/28 |
|---|---|---|---|
| 123294 | 10/1984 | European Pat. Off. | |
| WO87/06953 | 11/1987 | PCT Int'l Appl. | |
| 8600638 | 1/1986 | World Int. Prop. O. | 935/48 |

OTHER PUBLICATIONS

Gray et al., *Mol. Gen. Genet* 205: 127–133, 1986.
Pohlner et al., *Nature* 325:458–462, 1987.

*Primary Examiner*—Richard A. Schwartz
*Assistant Examiner*—S. Nolan
*Attorney, Agent, or Firm*—Seed and Berry

[57] ABSTRACT

Methods for producing heterologous proteins in a host organism whereby the proteins are processed through the secretory pathway of the host are provided. Secretion is achieved by transforming a host organism with a DNA construct comprising a transcriptional promoter operably linked to DNA sequences encoding a signal peptide, at least a portion of the BAR1 C-terminal domain capable of directing the export of heterologous proteins and a heterologous protein or polypeptide. DNA constructs and transformants are also provided wherein the DNA sequence encoding at least a portion of the C-terminal domain of BAR1 capable of directing the export of heterologous proteins further comprises a DNA sequence encoding a proteolytic cleavage site operably linked to the DNA sequence encoding a heterologous protein.

46 Claims, 23 Drawing Sheets

FIG. 1

```
                                                                          -680      -670
                                                                    TCTAGAAGAAC AAATTCACAA
     -650        -640        -630        -620        -610        -600        -590        -580        -570        -560
TGTGTCGTTG AGATACGGCA ACGAGTTGGA AGGTCGTAGC AAGGATCTAA TAAACAGATT TCATGTGGAA GATGAAAAGG ACATCTACGA GCGTAACCTAT TGCAACGAAA
     -540        -530        -520        -510        -500        -490        -480        -470        -460        -450
TGCTTTTGAA GTTGCTGATT GAGTAGACA GTATCGATTT GATTAACGTG GATGAGTCCT TAAGAAGGCC GTTGAAGGAA AAAAGGAAAG GCGTCATAAA GGAAATTCAG
     -430        -420        -410        -400        -390        -380        -370        -360        -350        -340
GCTATGTTAA AAAGTTGGA CTCTCTTAAA TAAGTTGTA TTTTTAGTTT ATAGATAACG GCTCTTGCCG AATTCATAGG CTGCACTCAT TCCGGTACGT ACACATTTGT
     -320        -310        -300        -290        -280        -270        -260        -250        -240        -230
TGCATTTATT ATATTAGAGA TGCGTTGTCC CTGTTTTTCT ACCTCCGACA TCATGCTGAA ACATGGCATG TAATTACCGT AAAAGGAAAT TACATGGGGA GTGTCACATA
     -210        -200        -190        -180        -170        -160        -150        -140        -130        -120
ATAGGCGACAA TAACATGTAT ACACAGCCAG CTATTCTGAA ACACACCACA TTATAGTTAT TGAATGTGTG TGTTTTTGA TAACAGTATA AAAGTGAAGA GAAAGCACGT
     -100         -90         -80         -70         -60         -50         -40         -30         -20         -10
CGAGCCTTGT CATGATGAAT TCTTTAATGA TCTTCGCGTG ATTTAATTCT AGTGGTTCGT ATCAATAAA ATCATACCAA AATAAAAGA GTGTCTAGAA GGGTCATATA

+1             10              20              30              40              50              60              70              80              90
ATG TCT GCA ATT AAT CAT CTT TGT TTG AAA CTT ATT TTG GCG AGT TTC GCG ATT ATT AAC ACC ATT ACT GCT TTA ACA AAC GAT GGC ACT
MET Ser Ala Ile Asn His Leu Cys Leu Lys Leu Ile Leu Ala Ser Phe Ala Ile Ile Asn Thr Ile Thr Ala Leu Thr Asn Asp Gly Thr
  1                    10                       20                                                                          30
           100             110             120             130             140             150             160             170             180
GGT CAC TTA GAA TTC CTT TTA CAA CAC GAA GAG ATG TAT TAC GCA ACA ACC TTA GAT ATA GGT ACA CCG TCC CAA AGT CTG ACA AGT GTG
Gly His Leu Glu Phe Leu Leu Gln His Glu Glu Met Tyr Tyr Ala Thr Thr Leu Asp Ile Gly Thr Pro Ser Gln Ser Leu Thr Val
            40                                                  50                                                           60
           190             200             210             220             230             240             250             260             270
TTG TTT GAT ACC GGA TCT GCC GAT TTT TGG GTT ATG GAT TCT AGC AGT TCT ATG CCC TTC TGC TTA CCA AAT ACG TCA TCC TAT TCA AAC
Leu Phe Asp Thr Gly Ser Ala Asp Phe Trp Val Met Asp Ser Ser Ser Met Pro Phe Cys Leu Pro Asn Thr Ser Ser Tyr Ser Asn
                     70                                                           80                                        *90
           280             290             300             310             320             330             340             350             360
GCA ACT TAT AAT GGC GAA GAA GTT AAG CCT TCA ATT GAT TGC AGG TCT ATG AGT ACT TAT AAT GAG CAT AGA TCT TCC ACC TAC CAA TAT
Ala Thr Tyr Asn Gly Glu Glu Val Lys Pro Ser Ile Asp Cys Arg Ser Met Ser Thr Tyr Asn Glu His Arg Ser Ser Thr Tyr Gln Tyr
                              100                                                           110                                                  120
           370             380             390             400             410             420             430             440             450
CTG GAA AAT GGT AGG TTT TAC ATC ACA TAT GCT GAC GGA ACA TTT GCT GAC GGT AGT GGG ACG GAA ACT GTA TCA ATT AAT GGA ATT
Leu Glu Asn Gly Arg Phe Tyr Ile Thr Tyr Ala Asp Gly Thr Phe Ala Asp Gly Ser Trp Gly Thr Val Ser Ile Asn Gly Ile
                              130                                                           140                                                  150
```

```
       460           470           480           490           500           510           520           530           540
GAC ATC CCC AAT ATC CAG TTC GGA GTT GCC AAG TAT GCT ACG ACA CCC GTT AGT GGT ATT GGG TTT CTT AGA AGA GAG TCC
Asp Ile Pro Asn Ile Gln Phe Gly Val Ala Lys Tyr Ala Thr Thr Pro Val Ser Gly Ile Gly Phe Leu Arg Arg Glu Ser
                    160                                       170                                       180

550           560           570           580           590           600           610           620           630
GTT AAG GGC TAT GAA GGT GCT CCT AAT TTT CCT AAT GAA TAT TAT CCT CAG ATT TTA AAA AGT GAA ATA ATC GAT GTG GTC GCG TCT
Val Lys Gly Tyr Glu Gly Ala Pro Asn Phe Pro Asn Glu Tyr Tyr Pro Gln Ile Leu Lys Ser Glu Lys Ile Ile Asp Val Val Ala Tyr
                    190                                       200                                       210

640           650           660           670           680           690           700           710           720
TCG CTG TTC TTA AAC TCA CCT GAT TCA GGT ACT GGT TTT GTT GCC ATT GAT GAA TCA AAG TTT TCT GGT GAT TTG TTC ACT
Ser Leu Phe Leu Asn Ser Pro Asp Ser Gly Thr Gly Ser Ile Phe Val Ala Gly Ala Ile Asp Glu Ser Lys Phe Ser Gly Asp Leu Phe Thr
                    220                                       230                                       240

730           740           750           760           770           780           790           800           810
TTC CCT ATG GTA AAT GAA TAT CCC ACA GTC GAC GCT CCT GCA ACT TTA GCA ATG ACT ATA CAA GGA TTA GGT GCC CAA AAC AAA AGT
Phe Pro Met Val Asn Glu Tyr Pro Thr Val Asp Ala Pro Ala Thr Leu Ala Met Thr Ile Gln Gly Leu Gly Ala Gln Asn Lys Ser
                    250                                       260                                       270

820           830           840           850           860           870           880           890           900
AGT TGT GAA CAT GAA ACG TTT ACG ACG AAG TAT CCA GTT TTG TTG GAC TCA GGA ACC TCG CTA ACC TTG AAT GCG CCC AAG GTC ATA GCA
Ser Cys Glu His Glu Thr Phe Thr Thr Lys Tyr Pro Val Leu Leu Asp Ser Gly Thr Ser Leu Leu Asn Ala Pro Lys Val Ile Ala
                    280                                       290                                       300

910           920           930           940           950           960           970           980           990
GAT AAA ATG GCT TCT TTT GTA AAT GCG TCC TAT AGT GAA GAG GAA GGT ATA TAT ATA TTA GAC TGT CCA GTA TCT GTA GGT GAC GTG GAA
Asp Lys Met Ala Ser Phe Val Asn Ala Ser Tyr Ser Glu Glu Glu Gly Ile Tyr Ile Leu Asp Cys Pro Val Ser Val Gly Asp Val Glu
                    310                                       320                                       330

1000          1010          1020          1030          1040          1050          1060          1070          1080
TAC AAT TTT GAT TTC GGC GAT TTG CAA ATA AGT GTT CCA CTG TCT AGT TTG ATT TTA CTG AGT CCC GAG ACA GAA GGC TAT TGT GGG TTT
Tyr Asn Phe Asp Phe Gly Asp Leu Gln Ile Ser Val Pro Leu Ser Ser Leu Ile Leu Leu Ser Pro Glu Thr Glu Gly Tyr Cys Gly Phe
                    340                                       350                                       360

1090          1100          1110          1120          1130          1140          1150          1160          1170
GCG GTC CAG CCA ACA AAC GAT TCG ATG GTT CTG GGT GAT GTG TTC CTG GGT GAT GTG TTC CTG CTG GGT GAT GTG TTC CTG GTA CTG GTG TTC CTG GTA TTC GAT CTC GAT AAT TAT AAG ATA
Ala Val Gln Pro Thr Asn Asp Ser Met Val Leu Gly Asp Val Phe Val Phe Leu Ser Ala Tyr Val Phe Asp Leu Asp Asn Tyr Lys Ile
                    370                                       380                                       390
```

FIG. 1 CONT.

```
      1180           1190           1200           1210           1220           1230           1240           1250           1260
TCT TTA GCA CAG GCA AAT TGG AAC AGC GAA GTT TCG AAA AAG CTA GTA AAT ATT CAA ACA GAT GGG TCT ATT TCA GGT GCC AAA ATT
Ser Leu Ala Gln Ala Asn Trp Asn Ser Glu Val Ser Lys Lys Leu Val Asn Ile Gln Thr Asp Gly Ser Ile Ser Gly Ala Lys Ile
                              400                                           410                                       420

1270           1280           1290           1300           1310           1320           1330           1340       1350
GCT ACA GCT GAA CCC TGG TCC ACC AAT GAA CCA TTT ACA GTC ACC TCT GAC ATT TAT TCA TCA ACA GGC TGC AAG AGT AGG CCT TTT CTT
Ala Thr Ala Glu Pro Trp Ser Thr Asn Glu Pro Phe Thr Val Thr Ser Asp Ile Tyr Ser Ser Thr Gly Cys Lys Ser Arg Pro Phe Leu
                              430                                           440                                       450

1360           1370           1380           1390           1400           1410           1420           1430       1440
CAA TCA TCG ACA GCC TCT TCG CTT ATT GCA GAA ACA CAA AGT CGC AAC TGC TCT ACG AAG ATG CCA GGC ACT AGA TCA ACT ACT
Gln Ser Ser Thr Ala Ser Ser Leu Ile Ala Glu Thr Gln Ser Arg Asn Cys Ser Thr Lys Met Pro Gly Thr Arg Ser Thr Thr
                              460                                           470                                   480

1450           1460           1470           1480           1490           1500           1510           1520       1530
GTC TTA AGT AAG CCT ACT ATG CAT CAA AAT AGT GCT GTC ACA GGT GCT GTC ACA CAA ACC TCA AAT GAA ACT AAA TTA GAA TTA TCC
Val Leu Ser Lys Pro Thr Met His Gln Asn Ser Ala Val Thr Gly Ala Val Thr Gln Thr Ser Asn Glu Thr Lys Leu Glu Leu Ser
                              490                                           500                                       510

1540           1550           1560           1570           1580           1590           1600           1610       1620
TCG ACT ATG GCA AAT TCG GGC AGT GTC CTC CCC ACT TCG AAT TCA ATA GAC AAA GAG TTC GAA CAT CAA TCT CAA ACT ACC AGC
Ser Thr Met Ala Asn Ser Gly Ser Val Leu Pro Thr Ser Asn Ser Ile Asp Lys Glu Phe Glu His Gln Ser Gln Thr Thr Ser
                              520                                           530                                   540

1630           1640           1650           1660           1670           1680           1690           1700       1710
GAT CCA AGT GTA GCG GAG CAT TCT ACG TTT AAC CAA ACG TTT GTA CAT CAT GAA ACT AAA TAT CGG CCT ACT CAT AAG ACA GTC ATA ACA GAA
Asp Pro Ser Val Ala Glu His Ser Thr Phe Asn Gln Thr Phe Val His His Glu Thr Lys Tyr Arg Pro Thr His Lys Thr Val Ile Thr Glu
                              550                                           560                                           570

1720           1730           1740           1750
ACT GTC ACG AAG TAT TCT ACA GTC TTA ATA AAT GTC TGT AAA CCA ACA TAT
Thr Val Thr Lys Tyr Ser Thr Val Leu Ile Asn Val Cys Lys Pro Thr Tyr
                              580

1760           1770           1780           1790           1800
TAAGAAAT CTGGAGTACA ATTTCTTTAT AGCATATAAA TATCAAATAT 1810           1820           1830           1840           1850           1860           1870           1880           1890           1900           1910
ATAGTCATTT TTAATACATG GAAAGCATAA TAAAAAAACA AGGGGAGTTT TACTGATATC ATTGGGATAT ATAAAACAAA ATAGTAATAT TATGCAGCCA TCACAATTTT 1920           1930           1940           1950           1960           1970           1980           1990           2000           2010           2020
GAACAAGTAG CACATTATTC ATTGAATAAA ATCTCCCCGA TGCTAAAAAA CGGGAATTG AACCCCCATC TGGCACGCGA CAAGCGCCCA TTCTGACCAT TAAACTATCA 2040           2050           2060
CGGAATATTA GATGTGATAC TGTTGTATTA CGGGCTCGAG
```

TGF SYNTHETIC STRATEGY

```
AATTCCTTGGATAAGAGAGTTGTTTCTCACTTCAACGACTCTCCAGACTGTCCACACCCAATTCTGTTCCACGGTACCTGTAGAT        ZC1732
         GGAACCTATTCTCAACAAAGAGTGAAGTTGCTGACAGGTCTGAGAGTGTGGGTTAAGACAAAGGTGCCATGGACATCTAAGAACC    ZC1733
         N  S  L  D  K  R  V  V  S  H  F  N  D  C  P  D  S  H  T  Q  F  F  H  G  T  C  R

TCTTGGTTCAAGAGACAAGCCAGCATGCGTTTGTCACTCTGGTTGGTGCTAGATGTGAACACGCTGACTTGTTGGCTTAAAT             ZC1198
       AAGTTCTCTGTTCGGTCGTACGCAAACAGTGAGCAAGCTACACTGTGCGACTGTACCGAATTAGATC                      ZC1200
       F  L  V  Q  E  D  K  P  A  C  V  C  H  S  G  Y  V  G  A  R  C  E  H  A  D  L  L  A
```

EGF SYNTHETIC STRATEGY

```
AATTCCTTGGATAAGAGAGAAACTCTGACTCTGAATGTCCATTGTCTCCACGACGGTTACTGTTGTTGCACGACGGTGTTGTATGTACATCGAAG    ZC1734
         GGAACCTATTCTCTTTGAGACTGAGAGTGTGCCAATGACAGAGTAACAGAGTGCTGCCACAAACGTGCTCCAAACATACATGTAGCTTCGAACC    ZC1735
         N  S  L  D  K  R  N  S  D  S  E  C  P  L  S  H  D  G  Y  C  L  H  D  G  V  C  M  Y  I  E

CCTTGGACAAGTACGCTTGTAACTGTGTTGTTGGTTACATCGGTGAAGATGTCAATACAGAGACTTGAAGTGGTGGGAATTGAGATAAAT         ZC1534
       TGTTCATGCGAACATTGACACAACCAATGTAGCACCTTCTACAGTTATGTCTCTGAACTTCACCACCCTTAACTCTATTTAGATC           ZC1535
       A  L  D  K  Y  A  C  N  C  V  V  G  Y  I  G  E  R  C  Q  Y  R  D  L  K  W  E  L  R
```

BAR1 SECRETION SIGNAL

This invention was made with Government support under grant No. PCM-8442440 awarded by the National Science Foundation. The Government has certain rights in this invention.

CROSS-REFERENCE TO RELATED APPLICATION

This application is a continuation-in-part to U.S. Ser. No. 229,074, filed Aug. 5, 1988, now abandoned which is a continuation-in-part to U.S. Ser. No. 104,316, filed Oct. 2, 1987, now abandoned.

DESCRIPTION

1. Technical Field

The present invention relates to the expression of proteins in general, and more particularly, to the use of specific secretion signals in the expression of proteins in yeast and mammalian cells.

2. Background Art

In recent years, advances in genetic engineering technology have shown that DNA sequences which are derived from genes of higher organisms and which encode specific proteins can be expressed in yeast cells. Recombinant DNA technology has also led to the discovery and utilization of secretion signals which allow specific proteins to be secreted through the cell wall into the medium.

The production of eukaryotic (e.g., mammalian) gene products in yeast has advantages over production using mammalian or bacterial cell culture. One of the major disadvantages in the use of bacteria as a host for the production of heterologous proteins is the production of endotoxins which must be completely removed before the product can be used as a pharmaceutical agent. Heterologous proteins produced in bacteria have been shown to have low solubility, a problem which, unless overcome, severely limits their use as pharmaceuticals. Further, the use of mammalian cells to express a protein product at commercial levels is much more expensive.

In contrast, commercial scale fermentation of yeast is well established, allowing for the production of large quantities of heterologous protein products. Yeast is a eukaryotic organism that shares greater similarity with mammalian cells than do bacteria. Yeast-produced proteins may also be secreted by the cells into the medium, where the reduced amount of contaminating protein facilitates the purification of the product. Secretion may also allow the glycosylation and disulfide bond formation that may be required for appropriate folding and/or biological activity of certain proteins. The secretory systems of yeast and mammalian cells are similar. Both cell types have secretory organelles, such as an endoplasmic reticulum, a Golgi apparatus, and a vesicle transit system to the cell surface. In addition, the secretory signal peptides found on nascent proteins are quite similar in the two cell types (Watson, *Nuc. Acids Res.* 12:5145, 1984), the key feature being a core of hydrophobic amino acids. These signal peptides are recognized by a set of proteins which deliver the newly synthesized secretory proteins to the endoplasmic reticular membrane and insert them into the lumen thereof. The signal peptides are substantially removed from the secretory proteins in both yeast and mammalian cells by signal proteases. For a review of eukaryotic secretory pathways, see Kelly (*Science* 230:25, 1985).

The secretion of heterologous proteins from yeast has been achieved through the use of natural yeast secretory peptides. Polypeptides known to be secreted from yeast contain a hydrophobic amino-terminal portion which allows the peptide to enter the secretion pathway. This hydrophobic region is known as a "signal peptide." The signal peptide generally acts in combination with other sequences to direct the secretion of the mature polypeptide or protein. These sequences are typically cleaved from the mature polypeptide during secretion and collectively constitute the secretory peptide. The α-factor secretory peptide (pre-pro sequence Kurjan and Herskowitz, *Cell* 30: 933–943, 1982) has been used by a variety of investigators to secrete heterologous proteins from yeast (Brake, EP 116,201, 1983; Bitter, EP 123,294, 1984; Singh, EP 123,544, 1984; Oshima et al., EP 171,000, 1985). Brake (EP 116,201, 1983) utilized the MFα1 promoter and secretory peptide to secrete human epidermal growth factor. Bitter (ibid.) used the MFα1 promoter and secretory peptide to secrete human [Leu5] β-endorphin. Singh (ibid.) cloned two genes, MFα1 and MFα2, whose products are capable of inducing G1 arrest in MATa cells. The MFα1 gene cloned by Singh was shown to correspond to the MFα1 gene described by Kurjan and Herskowitz (ibid.). The MFα2 gene was shown to be organizationally similar but not identical to the MFα1 gene. Singh used the MFα1 promoter and secretory peptide to secrete a variety of heterologous proteins. These include proteins which were secreted in significant amounts, such as human interferon D, human serum albumin, bovine interferon α1, bovine interferon α2, tissue plasminogen activator (t-PA) and human insulin-like growth factor; and proteins which were secreted in trace amounts, such as rennin and human interferon γ. Oshima et al. (ibid.) reported the use of the MFα1 promoter and secretory peptide to secrete α-neoendorphin and interleukin 2. They suggest the utilization of MFα1 in the secretion of other proteins or peptides, including insulin, somatostatin, growth hormone, growth hormone-stimulating factor, diuretic hormone, interferon γ, tumor necrosis factor and lymphotoxin.

Lemontt et al. (WO 86/00638, 1986) have used the PH05 secretory peptide to secrete heterologous proteins from yeast. Brake EP 123,289, 1984) has reported the use of the α-factor secretory peptide to secrete heterologous proteins.

The *S. cerevisiae* BAR1 gene encodes a protein known as "Barrier," which is secreted from matingtype a cells. The Barrier protein allows the cells to overcome the growth inhibitory effects of α-factor. The BAR1 secretion pathway may represent a different pathway from the α-factor secretion pathway.

MacKay et al. (U.S. Pat. No. 4,613,572, 1986) disclose that the BAR1 gene can be used to secrete foreign proteins, but do not identify specific regions of the gene that may be useful in this regard.

MacKay (WO 87/02670) discloses the use of the BAR1 signal peptide coding region to direct the secretion of low levels of foreign gene products from transformed yeast cells. The BAR1 secretory system described by MacKay (ibid.) was found to provide a less efficient secretion signal than the alpha-factor secretory peptide.

Studies of tissue plasminogen activator secretion from yeast indicate that the α-factor secretory peptide does not efficiently translocate t-PA or urokinase into the media. This may also prove to be true for other heterologous proteins.

Consequently, there is a need in the art for the identification of other secretory peptides that will allow foreign proteins to be secreted from yeast in a more efficient manner. The present invention fulfills this need, and further provides other related advantages.

DISCLOSURE OF THE INVENTION

Briefly stated, the present invention discloses a DNA construct comprising a transcriptional promoter operably linked to a DNA sequence encoding a signal peptide, followed in reading frame by a second DNA sequence encoding a portion of the BAR1 gene product, including at least a portion of the C-terminal domain and a heterologous protein or polypeptide. A preferred signal peptide is the Barrier signal peptide. In one embodiment, the second DNA sequence may comprise a segment encoding a heterologous protein or polypeptide followed downstream by a segment encoding at least a portion of the C-terminal domain of the BAR1 gene product. Alternatively, the second DNA sequence may comprise a segment encoding at least a portion of the C-terminal domain of the BAR1 gene product followed downstream by a segment encoding a heterologous protein or polypeptide.

In one aspect of the present invention, the portion of the C-terminal domain comprises the amino acid sequence of FIG. 1, beginning with serine, number 391, and ending with serine, number 526. Within a related aspect of the present invention, the portion of the C-terminal domain comprises the amino acid sequence of FIG. 1, beginning with alanine, number 423, and ending with serine, number 526.

In another aspect, the second DNA sequence further comprises a segment encoding a cleavage site positioned adjacent to the segment encoding a heterologous protein or polypeptide. Within preferred embodiments, the cleavage site is a dibasic cleavage site or a thrombin cleavage site.

In yet another aspect of the present invention, the second DNA sequence is mutagenized to prevent carbohydrate addition at one or both of amino acids 468 and 503 of the BAR1 gene product. Preferably, the second DNA sequence will encode a glutamine residue at position 468 and/or position 503.

The present invention may be used to express a variety of proteins, including urokinase, insulin, platelet-derived growth factor, epidermal growth factor, transforming growth factor α and analogs thereof. Within preferred embodiments, the transcriptional promoter is that of a gene encoding a triose phosphate isomerase (TPI) enzyme or an alcohol dehydrogenase (ADH) enzyme. Yeast cells and mammalian cells transformed with such a DNA construct are also disclosed.

In another aspect of the present invention, a method of producing a protein of interest is disclosed. The method generally comprises: (a) growing a host cell containing a DNA construct comprising a transcriptional promoter operably linked to a DNA sequence encoding a signal peptide followed in reading frame by a second DNA sequence encoding a heterologous protein or polypeptide and at least a portion of the C-terminal domain of the BAR1 gene product in an appropriate medium; and (b) isolating the protein or polypeptide product from the host cell. Preferred host cells include yeast cells and mammalian cells. The method may also include, after the step of isolating, purifying the protein product.

These and other aspects of the present invention will become evident upon reference to the following detailed description and attached drawings.

BRIEF DESCRIPTION OF THE DRAWINGS

FIG. 1 illustrates the nucleotide sequence of the BAR1 gene and the derived amino acid sequence of the primary translation product. Numbers above the lines refer to the nucleotide sequence; negative numbers indicate the 5' non-coding sequence. Numbers below the lines refer to the amino acid sequence. The putative signal peptide cleavage site is indicated by an arrow. Asterisks denote potential glycosylation sites.

FIG. 20 illustrates the EGF and TGFα coding sequences, together with the encoded amino acid sequences. Nucleotides and amino acids are represented by the standard one-letter codes.

BEST MODE FOR CARRYING OUT THE INVENTION

Figure 2:
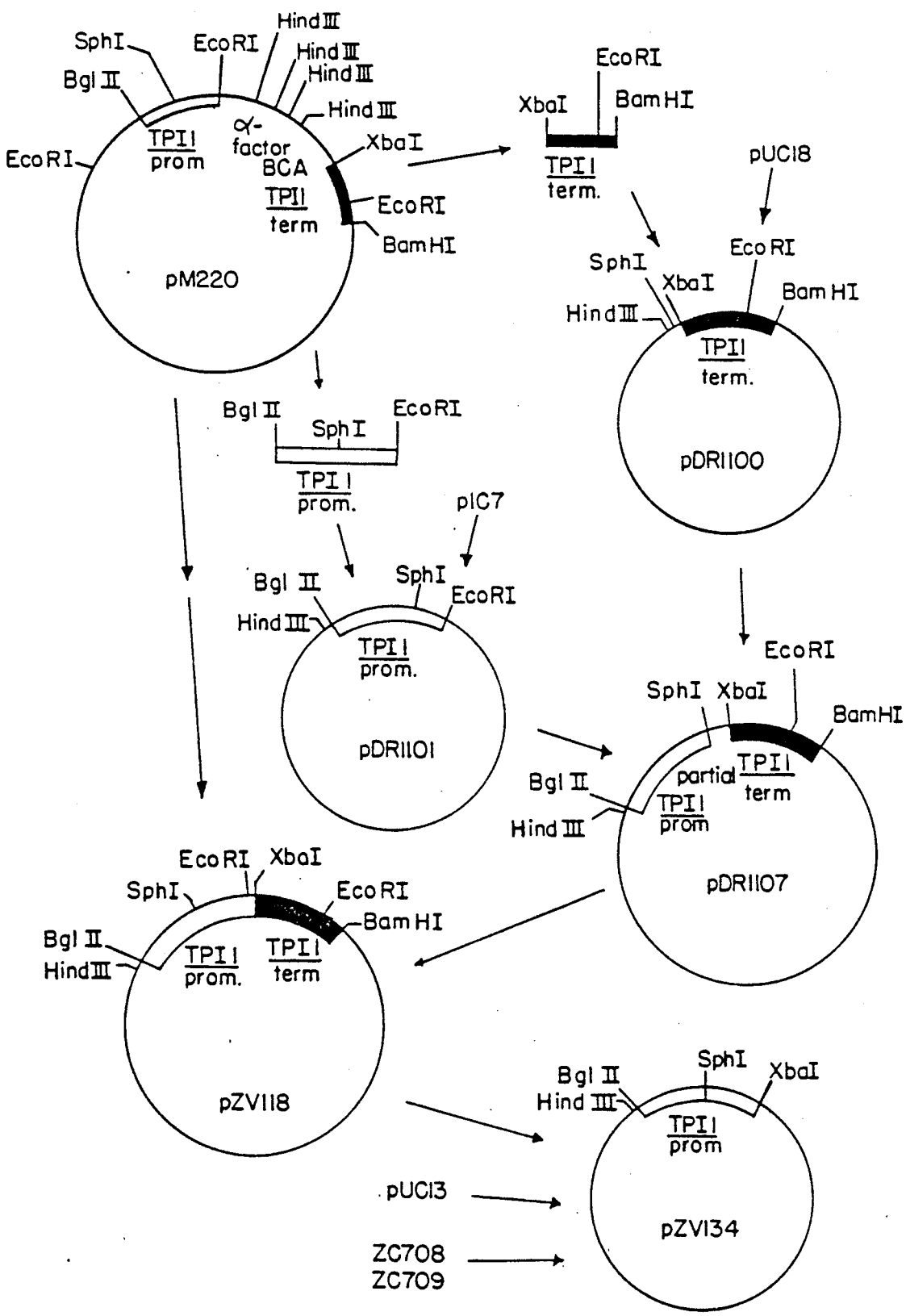
FIG. 2 illustrates the construction of plasmid pZV134.

As noted above, the present invention utilizes sequences encoding a portion of the C-terminal region (third domain) of the S. cerevisiae BAR1 gene product in conjunction with a sequence (signal sequence) encoding a signal peptide to direct the secretion of foreign proteins produced in a host cell. Together, the signal sequence and the sequence encoding a portion of the Barrier C-terminal region encode a hybrid secretory peptide. This hybrid secretory peptide is then used to direct the secretion of heterologous proteins or polypeptides from host cells. The signal peptide and third domain may be contiguous, with the foreign protein or polypeptide fused to the hybrid secretory peptide at its downstream (C-terminal) end, or the foreign protein or polypeptide may be placed between portions of the hybrid secretory peptide. In either arrangement, processing signals, preferably a dibasic cleavage site consisting of the amino acids Lys-Arg, Arg-Arg, Lys-lys or Arg-lys, may be used to effect cleavage between the secretory peptide and the heterologous protein. A preferred dibasic cleavage site is a KEX2 cleavage site, Lys-Arg. Alternatively, a thrombin cleavage site may be used as the processing site between the secretory peptide and the heterologous protein.

In a preferred embodiment, the hybrid secretory peptide consists essentially of a signal peptide and the C-terminal domain or a portion of the C terminal domain of Barrier. Sequences derived from the first and second domains of Barrier will be substantially absent. As discussed above, proteolytic processing signals may also be included.

Also as noted above, a preferred signal sequence is the BAR1 signal sequence, although other signal sequences, such as that of the S. cerevisiae PHO5 gene, may also be used. The precursor of the Barrier protein, encoded by the BAR1 gene, contains a putative signal peptide at its amino terminus. This putative signal peptide is characterized by a core of hydrophobic amino acids and is presumed to extend from amino acid 1 to amino acid 24 (FIG. 1). This portion of the BAR1 primary translation product is presumed to be removed during the processing of Barrier through the secretion pathway and is referred to herein as the "BAR1 signal peptide." The corresponding portion of the BAR1 gene is referred to herein as the "signal sequence."

Exemplary expression units include at least the BAR1 signal sequence and the third domain coding sequence, and may also include other BAR1 sequences. By way of example, one suitable expression unit comprises the TPI1 promoter (Kawasaki, U.S. Pat. No. 4,599,311, 1986), the BAR1 signal sequence, a portion of the sequence for the BAR1 C-terminal domain encoding amino acids 391 to 526, a sequence encoding a dibasic cleavage site, and the coding sequence for a heterologous protein, such as the DNA sequence coding for the insulin precursor MI-3 (also known as "B(1-29)-Ala-Ala-Lys-A(1-21)," as described by Markussen et al., EP 163,529).

Another exemplary expression unit comprises the TPI1 promoter, the BAR1 gene from the initiation ATG to the Eco RI site at +1572 bp, a sequence encoding a dibasic cleavage site, and the coding sequence for a heterologous protein, such as the DNA sequence coding for the insulin precursor MI-3.

Yet another exemplary expression unit comprises the TPI1 promoter, the yeast PHO5 (repressible acid phosphatase) signal sequence, a porcine urokinase cDNA, a portion of the BAR1 third domain sequence encoding amino acids 423 to 526, and the TPI1 terminator.

The alternative use of a thrombin cleavage site as the processing site between the secretory peptide and the heterologous protein yields other exemplary expression units. One such expression unit comprises the TPI1 promoter, the BAR1 signal sequence, the coding sequence for the BAR1 C-terminal domain, a sequence encoding a thrombin cleavage site (the amino acids proline and arginine), and the coding sequence for a heterologous protein, such as the DNA sequence coding for the insulin precursor MI-3.

An analysis of the BAR1 gene sequence has shown homology between Barrier and several pepsin-like proteases. In addition, Barrier contains a third domain at its C-terminus which does not show homology with these proteases. Further investigation by the inventors has shown that sequences within this domain are required for the export of Barrier from the cell. By combining the BAR1 putative signal sequence with the coding region for 136 amino acids of the third (C-terminal) domain, the inventors have obtained secretion levels for foreign proteins greater than those obtained using analogous constructs comprising the MFα1 pre-pro sequence.

In addition to using the 136 amino acid portion of the C-terminal domain, smaller segments of this domain may be used. Through the use of restriction enzyme cleavage and exonuclease digestion, smaller fragments of the third domain are generated and tested for their ability to direct the secretion of proteins from transformed cells. For example, in one series of experiments, the BAR1 gene was cleaved at several convenient restriction sites to generate C-terminal deletions. The resultant gene fragments were then fused to a fragment encoding the C-terminal portion of substance P (Munro and Pelham, EMBO J. 3:3087-3093, 1984). The resultant fusion proteins could be detected and quantitated using an antibody to substance P. These studies indicated that the region from position 1267 (FIG. 1) to the Eco RI site at position 1572 may be combined with a suitable signal peptide coding sequence to provide a strong hybrid secretory peptide.

It may also be advantageous to generate expression units containing mutants of the BAR1 third domain such that the N-linked glycosylation sites at amino acids 468 through 470 (glycosylation site #7), or amino acids 503 through 505 (glycosylation site #8), or at both sites are mutagenized to prevent carbohydrate addition at amino acid 468 or 503, respectively. N-linked glycosylation occurs at the acceptor tripeptide sequences of Asn-X-Ser or Asn-X-Thr, where X may be any amino acid, although not all of these tripeptide sequences are host to N-linked glycosylation. DNA sequences encoding N-linked glycosylation acceptor sites may be mutagenized to prevent the addition of carbohydrate moieties by substituting alternative amino acid codons at any of the sites of the tripeptide acceptor sequence. For example, a proline residue in the second position of either of the acceptor sequences Asn-X-Ser or Asn-X-Thr may prohibit glycosylation in yeast (Marshall, Biochem. Soc. Symp. 40:17-26, 1974). The third amino acid of the acceptor tripeptide sequence may also be changed. In a particularly preferred embodiment, the asparagine residue in the first position of the tripeptide acceptor sequence is replaced with another amino acid. Most preferably, a glutamine residue (Gln) is substituted for the Asn residue. However, other amino acid substitutions may also be made at any of the three positions of the tripeptide acceptor sequence to prevent carbohydrate addition.

Mutations which prohibit the N-linked addition of carbohydrate moieties at either site #7 or #8, or at both sites, are preferably produced by site directed in vitro mutagenesis. A particularly preferred mutation causes a substitution of a Gln residue for an Asn residue in the first position of a tripeptide acceptor sequence. By generating BAR1 third domain glycosylation site mutants at position #7 or #8, the inventors have obtained secretion levels for foreign proteins greater than those obtained using analogous constructs comprising the MFα1 pre-pro sequence or the BAR1 signal peptide and BAR1 third domain with wild-type glycosylation. In a growth curve comparison between cells transformed with BAR1 constructs containing glycosylation site mutations at position #7 or #8 and cells transformed with fully glycosylated BAR1 constructs, the growth lag apparent in fully glycosylated BAR1 construct transformants is lacking in the mutagenized construct transformants.

Expression units of the present invention containing a dibasic cleavage site are preferably produced by ligating a suitable promoter, the appropriate portion of the BAR1 gene, an adapter coding for a dibasic cleavage site, the heterologous gene or cDNA, and a transcriptional terminator, such as the TPI1 terminator. The expression units of the present invention containing a thrombin cleavage site are preferably produced by in vitro mutagenesis of the dibasic processing site contained in the above-mentioned expression units, for example, by changing the Lys-Arg to a Pro-Arg, or by assembling the expression unit with an adapter encoding the thrombin cleavage site.

The resultant expression units are then ligated into a suitable vector. Suitable yeast vectors include YRp7 (Struhl et al., *Proc. Natl. Acad. Sci. USA* 76: 1035–1039, 1978), YEp13 (Broach et al., *Gene* 8:121–133, 1979), pJDB248 and pJDB219 (Beggs, *Nature* 275:104–108, 1978) and derivatives thereof. Such vectors will generally include a selectable marker, such as the nutritional marker LEU2, which allows selection in a host strain carrying a leu2 mutation, or the glycolytic gene POT1, from *Schizosaccharomyces pombe* (Kawasaki and Bell, EP 171,142), which allows selection in a host strain carrying a tpi1 mutation. Preferred promoters include those from yeast glycolytc genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals*, Hollaender et al. (eds.), p. 355, Plenum, N.Y., 1982; Ammerer, *Meth. Enzymol.* 101: 192–201, 1983). In this regard, a particularly preferred promoter is the TPI1 promoter (Kawasaki, U.S. Pat. No. 4,599,311, 1986). A preferable transcriptional termination signal is the TPI1 terminator.

The constructs comprising the expression unit in a yeast vector are transformed into yeast, such as strains of *Saccharomyces cerevisiae*. Techniques for transforming yeast are well known in the literature, and have been described, for instance, by Beggs (ibid.) and Hinnen et al. (*Proc. Natl. Acad. Sci. USA* 75:1929–1933, 1978). The transformants are cultured in appropriate media containing carbon and nitrogen sources, as well as other nutrients which may be required by the particular host strain. Host cells transformed with plasmids containing the POT1 selectable marker may be cultured in complex media containing glucose as a carbon source.

Yeast strains suitable for use in the present invention will have a genetic defect which can be complemented by a plasmid-borne selectable marker. Selectable markers are commonly genes which complement auxotrophy in the host cell. Yeast strains having such defects are widely available, such as from American Type Culture Collection, Rockville, Md., or the Yeast Genetic Stock Center, Berkeley, Calif., or may be prepared using standard techniques of mutation and selection. Choice of a particular host and selectable marker is well within the level of ordinary skill in the art. To optimize production of heterologous proteins, it is preferred that the host strain carries a mutation, such as the pep4 mutation (Jones, *Genetics* 85:23, 1977), which results in reduced proteolytic activity.

Mammalian cell expression vectors are also well known in the art. A variety of promoters are available, including viral (e.g., SV40 and adenovirus) and cellular (e.g., metallothionein gene; Karin, U.S. Pat. No. 4,601,978; and Palmiter et al., U.S. Pat. No. 4,579,821) promoters. Other elements, including transcription termination signals, polyadenylation signals and transcriptional enhancer sequences, are selected for their function in the particular host cell line. Methods for transfecting mammalian cells and expressing cloned DNA sequences are described by Kaufman and Sharp (*J. Mol. Biol.* 159:601–621, 1982), Southern and Berg (*J. Mol. Appl. Genet.* 1:327–341, 1982), Loyter et al. (*Proc. Natl. Acad. Sci. USA* 79:422–426, 1982), and Neumann et al. (*EMBO J.* 1:841–845, 1982). The cells are cultured in serum-containing or serum free media containing appropriate supplements. Suitable media are available from commercial suppliers or may be prepared according to published recipes (see, e.g., catalogs of the American Type Culture Collection).

Proteins produced according to the present invention may be purified by conventional methods. Particular purification protocols will be determined by the nature of the specific protein to be purified. Such determination is within the ordinary level of skill in the art. Generally, the cell culture medium will be separated from the cells and the protein will be isolated from the medium. Useful purification techniques include precipitation, immunoadsorption and fractionation by a variety of chromatographic methods, including ion exchange chromatography, affinity chromatography and gel filtration.

EXAMPLES

Example 1: Cloning of the BAR1 Gene From *S. cerevisiae*

The BAR1 gene was cloned as described by MacKay et al. (U.S. Pat. No. 4,613,572, 1986). Briefly, a pool of plasmids containing a random mixture of yeast genomic DNA fragments derived from *S. cerevisiae*, in the vector YEp13, was transformed into a yeast strain with the genotype MATa leu2 bar1. Transformants were selected for their ability to grow on synthetic media lacking leucine. The transformed cells were further screened for the ability of the cloned DNA to complement the bar1 defect in the host cell. Yeast MATa cells that lack a functional BAR1 gene are abnormally sensitive to inhibition by α-factor. Yeast transformants which were found to be resistant to α-factor inhibition were then screened for the ability to secrete Barrier activity. Plasmid pBAR2 (ATCC #3940), comprising the vector YEp13 and a 9.2 kb yeast genomic insert, was found to fully complement the bar1 defect.

The BAR1 gene and its associated flanking sequences were subcloned into the vector pUC13 (Vieira and Messing, *Gene* 19:259, 1982) as a Hind III-Xho I fragment. Plasmid pBAR2 was digested with Hind III and Xho I to isolate the approximately 3 kb fragment containing the BAR1 gene. Plasmid pUC13 was linearized by digestion with Hind III and Sal I. The linearized vector was ligated with the 3 kb fragment from pBAR2. The resultant plasmid was designated pZV9 (deposited as a transformant in *E. coli* strain RRI, ATCC #53283).

The sequence of the cloned BAR1 gene and the amino acid sequence of the primary translation product are shown in FIG. 1.

Example 2: Subcloning the TPI1 Promoter and Terminator

Referring to FIG. 2, plasmid pM220 (also known as pM210) was used as the source of both the TPI1 promoter and terminator (Alber and Kawasaki, *J. Mol. Appl. Gen.* 1:419–434, 1982). *E. coli* RR1 transformed with pM220 has been deposited with ATCC under accession number 39853. Plasmid pDR1107, comprising the TPI1 promoter and terminator, was constructed by first subcloning the 900 bp Bgl II-Eco RI TPI1 promoter fragment of pM220 into pIC7 (Marsh et al., *Gene* 32:481–485, 1984) to generate plasmid pDR1101. Plasmid pDR1101 was then digested with Hind III and Sph I to isolate the 700 bp partial TPI1 promoter fragment. Plasmid pDR1100, comprising the 800 bp Xba I-Bam HI TPI1 terminator fragment of pM220 subcloned into pUC18, was cut with Hind III and Sph I. The 700 bp partial TPI1 promoter was ligated into linearized pDR1100 to produce pDR1107. The TPI1 promoter from pM220, modified to insert an Xba I site at the 3' end of the promoter sequence, was used to replace the TPI1 promoter present in pDR1107. Plasmid pM220 was digested with Eco RI, and the 0.9 kb fragment comprising the TPI1 promoter was isolated by agarose gel electrophoresis and the ends were blunted with DNA polymerase I (Klenow fragment). Kinased Xba I linkers were added to the fragment, which was then digested with Bgl II and Xba I. This modified TPI1 promoter fragment was then ligated into the 3.4 kb Bgl II-Xba I vector fragment of pDR1107 to produce pZV118.

The Eco RI site which was regenerated at the 3' end of the TPI1 promoter in pZV118 was then destroyed. The plasmid was digested with Hind III and Eco RI, and the 0.9 kb fragment was isolated and ligated to a synthetic linker constructed by annealing oligonucleotides ZC708 (5'AATTGCTCGAGT3') and ZC709 (3'CGAGCTCAGATC5'). (Oligonucleotides were synthesized on an Applied Biosystems model 380A DNA synthesizer and purified by polyacrylamide gel electrophoresis.) ZC708 and ZC709 were kinased and annealed by the method described by Maniatis et al. (*Molecular Cloning, A Laboratory Method,* p. 122, Cold Spring Harbor Laboratory, Cold Spring Harbor, N.Y., 1982). The adapter addition eliminates the Eco RI site at the 3' terminus of the TPI1 promoter fragment and adds Xho I and Xba I sites. This fragment was then joined to Hind III-Xba I-cut pUC13. The resultant plasmid was designated pZV134 (FIG. 2).

Example 3: Construction of Plasmid pGLY2,3

Figure 3:
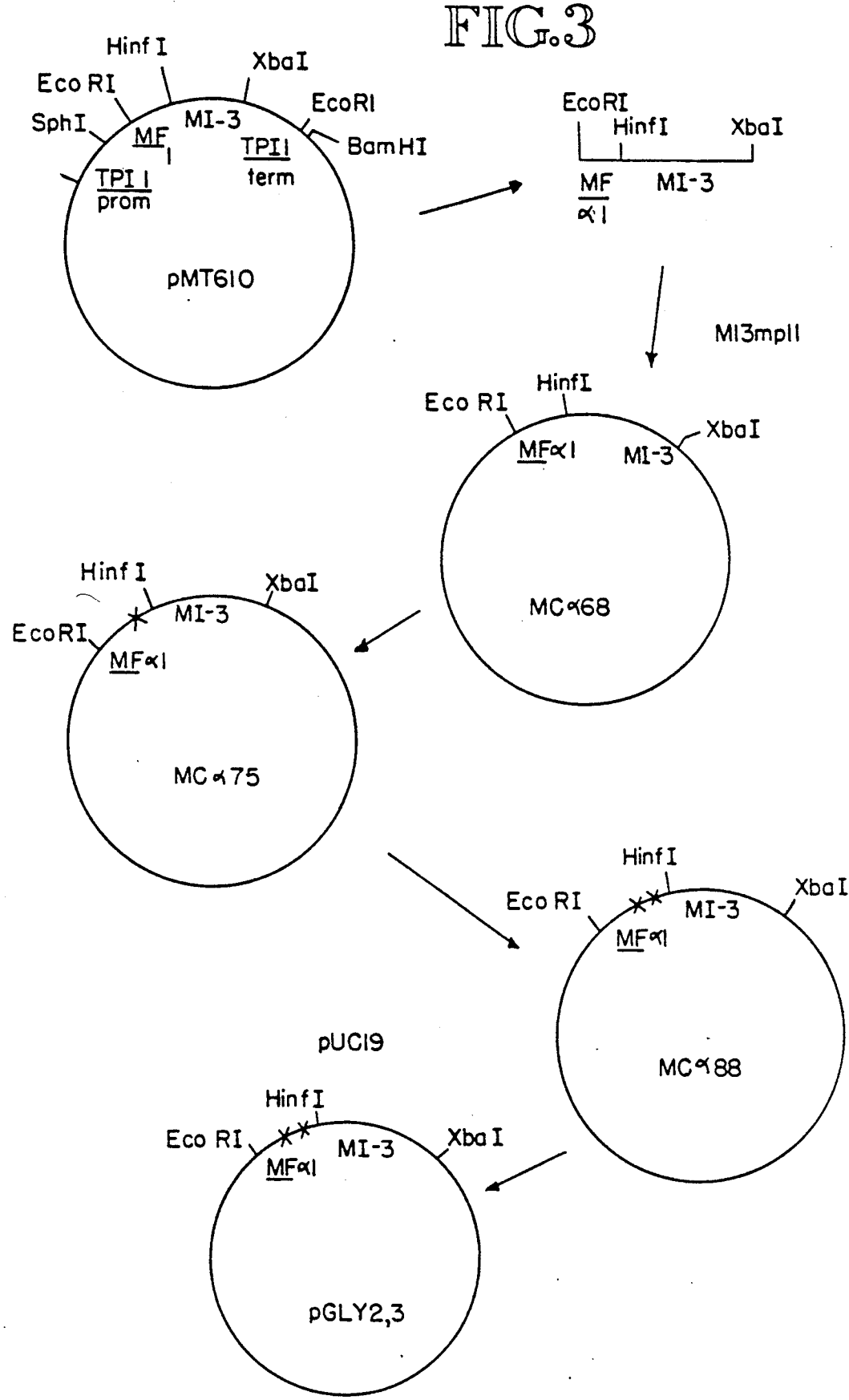
FIG. 3 illustrates the construction of plasmid pGLY2,3.

A 0.5 kb fragment comprising the yeast codonoptimized sequences encoding the MFα1 leader and the insulin precursor MI-3 (also known as B(1-29)-Ala-Ala-Lys-A(1-21), derived from plasmid pMT610 (Markussen et al., EP 163,529; see FIG. 3), was mutagenized to remove two potential glycosylation sites present in the MFα1 leader. The sites, beginning at amino acid 57 (glycosylation site #2) and at amino acid 67 (glycosylation site #3) of the MFα1 leader, were removed by changing an Asn codon to a Gln codon in each case. For mutagenesis, the 0.5 kb Eco RI-Xba I MFα1 fragment derived from pMT610 was ligated into M13mp11, which had been linearized by digestion with Xba I and Eco RI. The resultant recombinant phage was designated mCα68. Oligonucleotides ZC457 (5'TGT TTA TCC AAA CTA CTA TTG CC3') and ZC458 (5'GCC ATT TTC CCA ATC CAC CAA T3') were synthesized on an Applied Biosystems model 380A DNA synthesizer and purified by polyacrylamide gel electrophoresis. The Asn codon of the MFα1 leader glycosylation site #3 was then altered by in vitro mutagenesis (Zoller and Smith, *DNA* 3:479–488, 1984; and Zoller and Smith, *Meth. Enzymology* 100:468–500, 1983 using oligonucleotide ZC457 and the mCα68 template. Positive clones were sequenced, and a correct clone was designated mCα75. Oligonucleotide ZC458, which altered the MFα1 glycosylation site #2, was used to mutagenize the mCα75 template using the mutagenesis method described by Zoller and Smith (ibid.). positive clones were sequenced, and a correct clone was designated mCα88. The 0.515 kb Eco RI-Xba I fragment comprising the mutagenized MFα1 leader and the gene encoding MI-3 was removed from mCα88 and subcloned into pUC19 which had been linearized by digestion with Eco RI and Xba I. The resultant plasmid was designated pGLY2,3 (FIG. 3).

Example 4: Construction of Expression Vector pSW167

The expression vector pSW167 comprises the sequence encoding the first 526 amino acids of Barrier fused to the MI-3 coding sequence in the yeast vector YEp13. An expression unit was constructed using the TPI1 promoter and a fusion between a 1578 bp BAR1 fragment and the coding sequence for MI-3, using an adapter encoding a dibasic cleavage site to join, in frame, the two sequences. In constructing the fusion, the BAR1 coding sequence was obtained from pSW8 and its derivative pSW81, which were constructed as follows.

Figure 4:
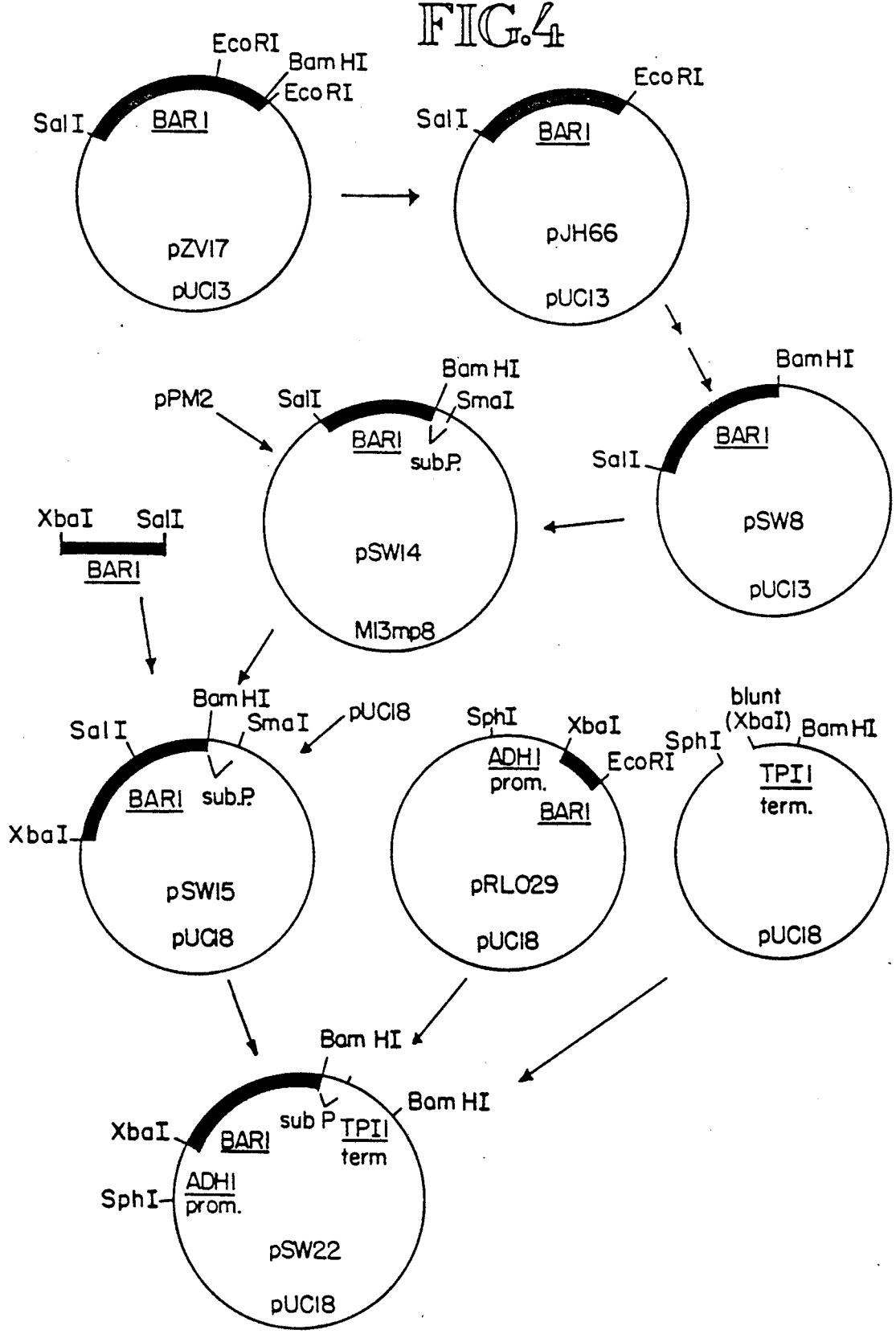
FIG. 4 illustrates the construction of plasmid pSW22.

Plasmid pZV9, comprising the entire BAR1 coding region and its associated flanking regions, was cut with Sal I and Bam HI to isolate the 1.3 kb BAR1 fragment. This fragment was subcloned into pUC13, which had been cut with Sal I and Bam HI, to generate the plasmid designated pZV17 (FIG. 4). Plasmid pZV17 was digested with Eco RI to remove the 3'-most 0.5 kb of the BAR1 coding region. The vector-BAR1 fragment was re-ligated to create the plasmid designated pJH66. Plasmid pJH66 was linearized with Eco RI and blunt-ended with DNA polymerase I (Klenow fragment). Kinased Bam HI linkers (5'CCGGATCCGG3') were added, and excess linkers were removed by digestion with Bam HI before re-ligation. The resultant plasmid was designated pSW8 (FIG. 4).

Figure 5:
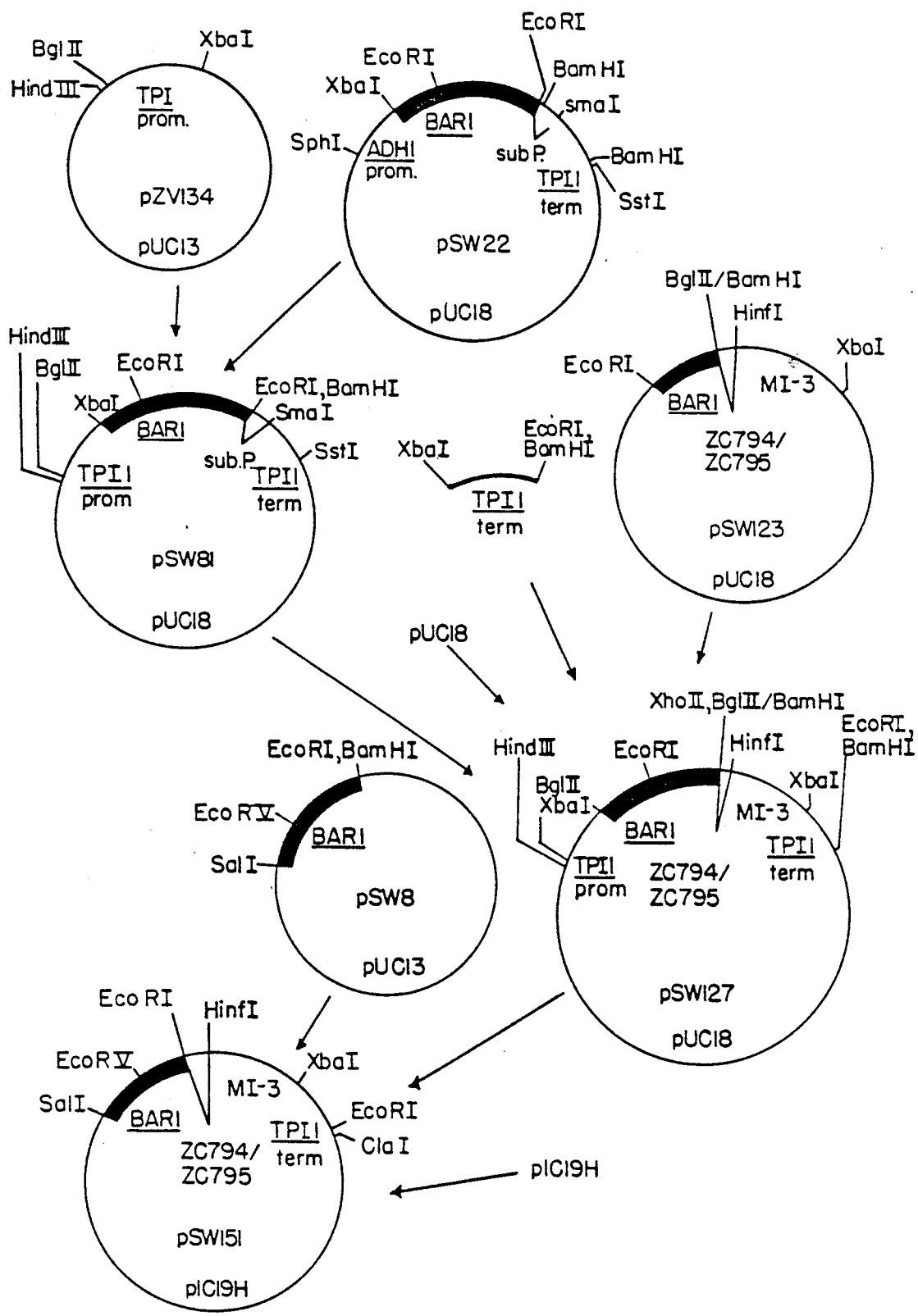
FIG. 5 illustrates the construction of plasmid pSW151.

Plasmid pSW81, comprising the TPI1 promoter, the BAR1 coding region fused to the coding region of the C-terminal portion of substance P (Munro and Pelham, ibid.), and the TPI1 terminator, was derived from pSW8 as shown in FIGS. 4 and 5. Plasmid pSW8 was cut with Sal I and Bam HI to isolate the 824 bp fragment encoding amino acids 252 through 526 of Barrier. Plasmid pPM2, containing the synthetic oligonucleotide sequence encoding the dimer form of the C-terminal portion of substance P in M13mp8, was obtained from Munro and Pelham. Plasmid pPM2 was linearized by digestion with Bam HI and Sal I and ligated with the 824 bp BAR1 fragment from pSW8. The resultant plasmid, pSW14, was digested with Sal I and Sma I to isolate the 871 bp BAR1-substance P fragment. Plasmid pZV16, comprising a fragment of BAR1 encoding amino acids 1 through 250, was cut with Xba I and Sal I to isolate the 767 bp BAR1 fragment. This fragment was ligated with the 871 bp BAR1 substance P fragment in a three-part ligation with pUC18 cut with Xba I and Sma I. The resultant plasmid, designated pSW15, was digested with Xba I and Sma I to isolate the 1.64 kb BAR1-substance P fragment. The ADH1 promoter was obtained from pRL029, comprising the ADHI promoter and 116 bp of the BAR1 5' coding region in pUC18 (MacKay, WO 87/02670). Plasmid pRL029 was digested with Sph I and Xba I to isolate the 0.42 kb ADH1 promoter fragment. The TPI1 terminator (Alber and Kawasaki, ibid.) was provided as a blunted Xba I-Sph I fragment comprising 0.7 kb of the TPI1 terminator (blunted Xba I to Eco RI) linked to pUC18 (Eco RI-Sph I). This fragment was ligated with the 0.42 kb ADH1 promoter fragment and the 1.64 kb BAR1-substance P fragment in a three-part ligation to produce plasmid pSW22 (FIG. 4).

The ADH1 promoter present in plasmid pSW22 was replaced with the TPI1 promoter to construct plasmid pSW81 (FIG. 5). The TPI1 promoter was provided as a 900 bp Hind III-Xba I fragment. The 2.3 kb fragment containing the BAR1-substance P fusion and the TPI1 terminator was isolated from plasmid pSW22 as an Xba I-Sst I fragment. The TPI1 promoter fragment and the BAR1-substance P-TPI1 terminator fragment were joined in a three-part ligation with pUC18 which had been linearized with Hind III and Sst I. The resultant plasmid was designated pSW81.

The fusion between BAR1 and MI-3 was made using a synthetic oligonucleotide adapter encoding a Lys-Arg cleavage site. Oligonucleotides ZC794 (5'GAT CCT TGG ATA AAA G3') and ZC795 (5'AAT CTT TTA TCC AAG3'), were kinased and annealed to produce an adapter comprising Bam HI and Hinf I adhesive ends and a sequence encoding the Lys-Arg cleavage site. Plasmid pGLY2,3 (Example 3) was cut with Eco RI and Xba I to isolate the 0.515 kb fragment containing the modified MFα1 pre-pro and Ml-3 sequences. This fragment was then cut with Hinf I to liberate the 180 bp MI-3 fragment. Plasmid pSW22, described above, was cut with Eco RI and Bgl II to isolate the 240 bp BAR1 fragment. This fragment was joined with the 180 bp MI-3 fragment and the ZC794/ZC795 adapter in a four-part ligation with pUC18 linearized with Eco RI and Xba I. The resultant plasmid, designated pSW123 (illustrated in FIG. 5), was cut with Eco RI and Xba I to isolate the 0.2 kb BAR1-MI-3 fragment. Plasmid pSW81 was cleaved with Hind III and Eco RI to isolate the 1.1 kb TPI promoter-BAR1 fragment. The TPI1 terminator was provided as a 0.76 kb Xba I-Bam HI fragment. The 1.1 kb TPI1 promoter-BAR1 fragment, the 0.2 kb BAR1-MI-3 fragment, and the TPI1 terminator fragment were joined in a four-part ligation with pUC18 which had been linearized with Hind III and Bam HI. The resultant plasmid, designated pSW127, contains the TPI1 promoter, the BAR1 sequence encoding amino acids 1-115, a sequence encoding a Lys-Arg cleavage site, the MI-3 coding sequence, and the TPI1 terminator.

Plasmid pSW151 was constructed to replace the BAR1 coding region present in pSW127 with the coding region for amino acids 251-526 from the BAR1 gene (FIG. 5). Plasmid pSW127 was digested with Xho II and Eco RI to isolate the 965 bp fragment comprising the ZC794/ZC795 synthetic adapter fused to MI-3 coupled with the TPI1 terminator. Plasmid pSW8 was digested with Sal I and Bam HI to isolate the 821 bp fragment encoding the C-terminal 275 amino acids of BAR1. Plasmid pIC19H (Marsh et al., ibid.), linearized with Sal I and Eco RI, was joined with the 965 bp and 821 bp fragments in a three-part ligation. The resultant plasmid was designated pSW151.

Figure 6:
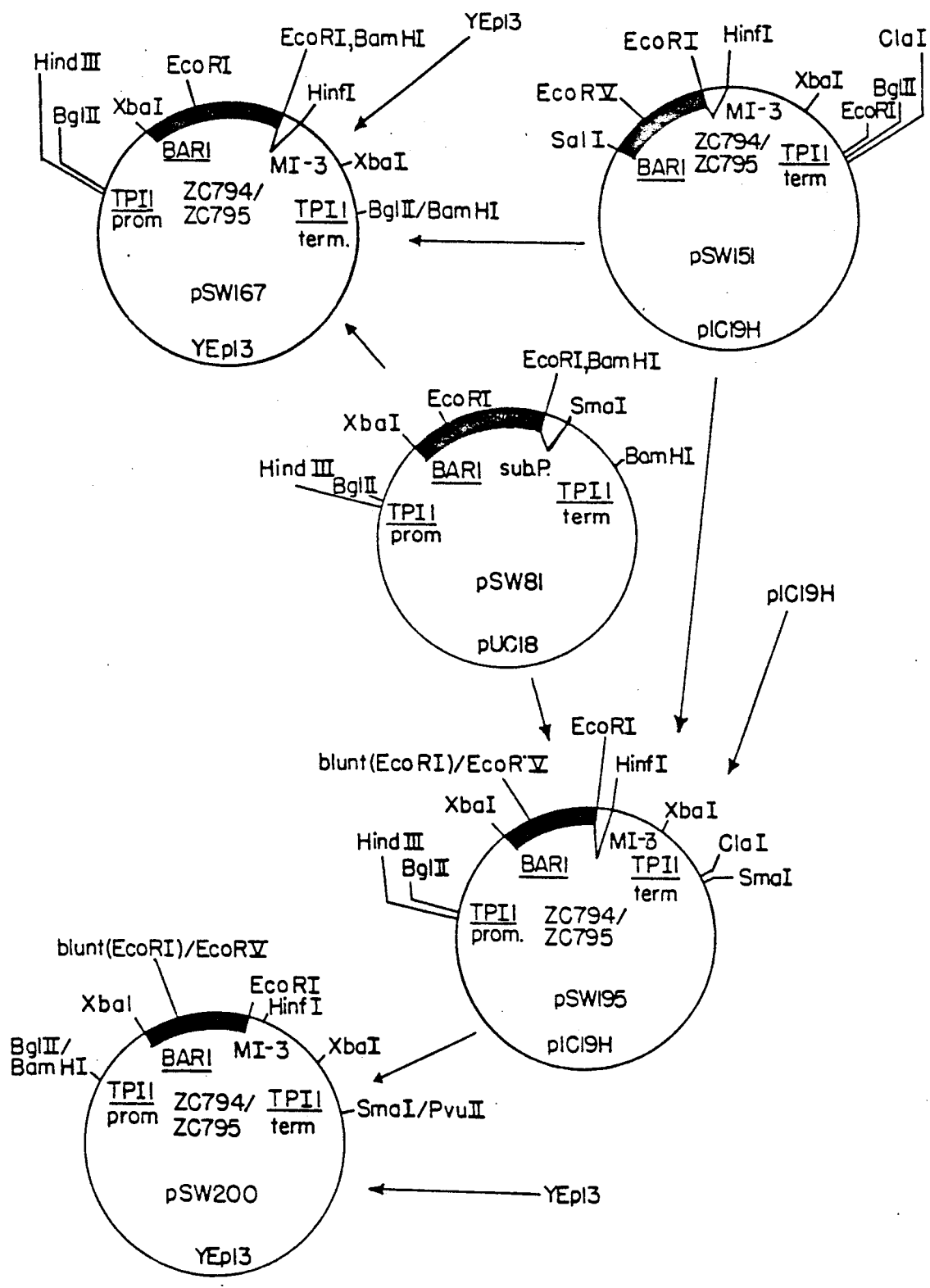
FIG. 6 illustrates the construction of the expression vectors pSW167 and pSW200.

Plasmid pSW167, comprising codons 1 through 526 of BAR1 fused to the Ml-3 sequence in the yeast vector YEp13, was constructed as follows. Plasmid pSW81 provided the TPI1 promoter and the BAR1 sequence required to complete the coding sequence for BAR1 when joined to the BAR1 sequence present in pSW151. Plasmid pSW81 was digested with Hind III and Sal I to isolate the 1.67 kb TPI1 promoter-BAR1 fragment. Plasmid pSW151 was cleaved with Sal I and Bgl II to isolate the 1.61 kb fragment comprising the BAR1-MI-3 fusion and the TPI1 terminator. This fragment was joined with the 1.67 kb TPI1 promoter-BAR1 fragment and YEp13 (Broach et al., Gene 8:121–133, 1979) which had been linearized with Hind III and Bam HI. The resultant plasmid was designated pSW167 (FIG. 6). Plasmid pSW167 has been deposited with American Type Culture Collection as an *E. coli* HB101 transformant under Accession Number 67523.

Example 5: Construction of Expression Vector pSW200

A construct comprising the BAR1 signal sequence, the BAR1 third domain sequence, and the MI-3 coding sequence was first assembled in the vector pIC19H (Marsh et al., ibid.), then cloned into the yeast vector YEp13 (FIG. 6). Plasmid pSW81 (Example 4) was linearized with Eco RI. The Eco RI adhesive ends were filled in by treatment with DNA polymerase I (Klenow fragment). The resultant blunt-ended fragment was then cut with Bgl II to isolate the 1.1 kb fragment comprising the TPI1 promoter and the BAR1 signal sequence. Plasmid pSW151 (Example 3) was cut with Eco RV and Cla I to isolate the 1.37 kb fragment comprising the 403 bp BAR1 third domain sequence, the MI-3 coding sequence, and the TPI1 terminator. This fragment was joined with the 1.1 kb fragment derived from pSW81 in a three-part ligation with pIC19H which had been linearized by digestion with Bgl II and Cla I. The resultant plasmid, designated pSW195, was digested with Bgl II and Sma I to isolate the 2.4 kb expression unit, which was then ligated into YEp13 which had been linearized by digestion with Bam HI and Pvu II. The resultant plasmid was designated pSW200. Plasmid pSW200 has been deposited with American Type Culture Collection as an *E. coli* HB101 transformant under Accession Number 67524.

Example 6: Construction of Vector pSW207

Figure 7:
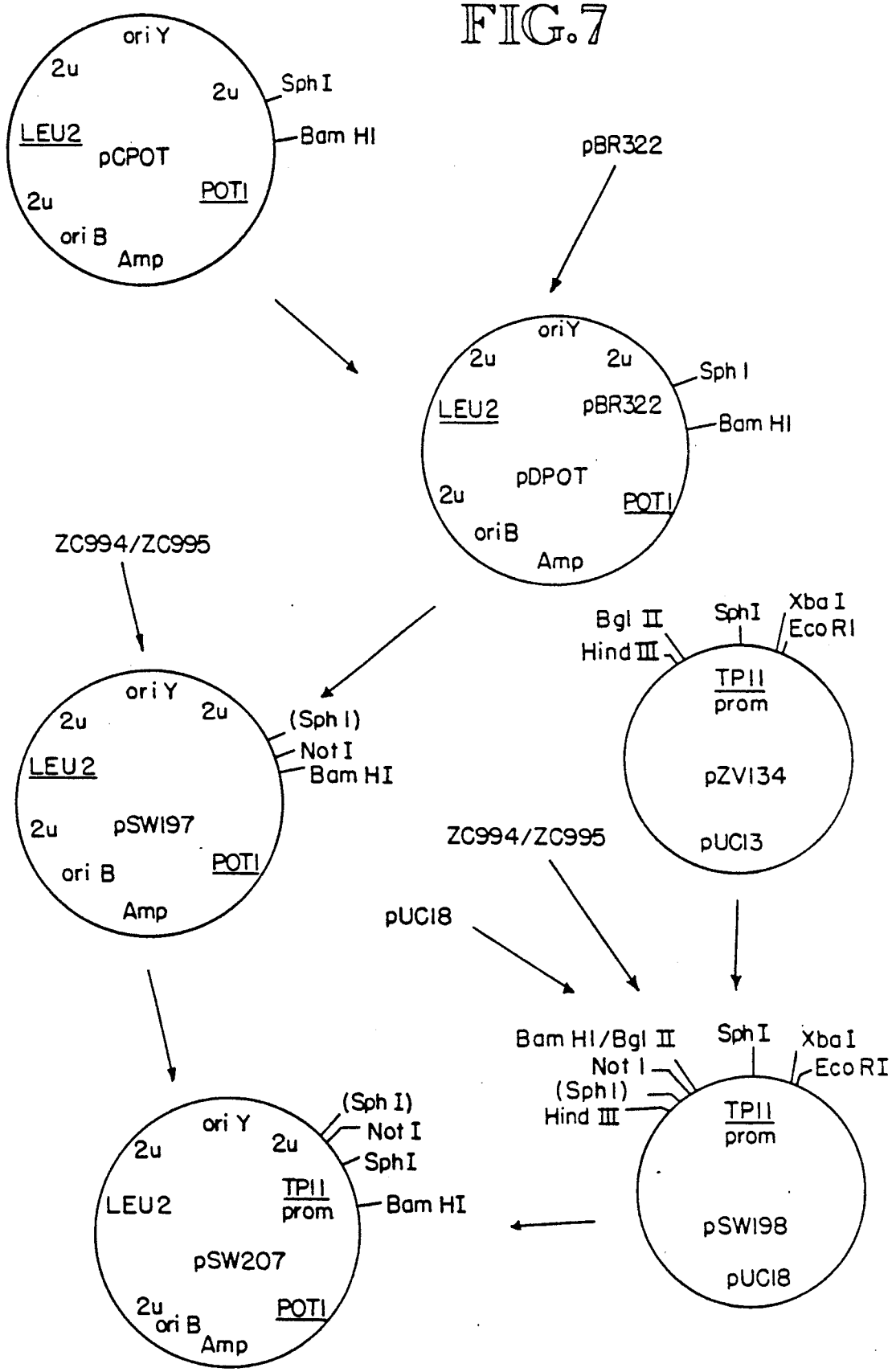
FIG. 7 illustrates the construction of plasmid pSW207.

The expression unit contained in pSW167 was also placed into a vector employing the *S. pombe* POT1 gene as the selectable marker to complement a tpi1 deficiency in the host cell. The POT1 gene allows only low-level compensation for the tpi1 defect in the yeast host strain. This low-level compensation produces a compensating increase in the copy number of the expression vector. This vector was derived from the vector pCPOT (deposited with ATCC as an *E. coli* strain HB101 transformant, Accession No. 39685). As shown in FIG. 7, the vector pCPOT was altered by replacing the 750 bp Sph I-Bam HI fragment containing 2 micron and pBR322 sequences with a 186 bp Sph I-Bam HI fragment derived from the pBR322 tetracycline resistance gene, to construct plasmid pDPOT. Plasmid pDPOT was modified to destroy the Sph I site and place a Not I site 5' to the Bam HI site. Oligonucleotides ZC994 (5'GAT CCG CGG CCG CAC ATG3') and ZC995 (5'TGC GGC CGC G3') were kinased and annealed to form an adapter with a 5' Sph I-compatible end, a Not I site, and a 3' Bam HI adhesive end. Plasmid pDPOT was linearized by digestion with Sph I and Bam HI. The linearized pDPOT was ligated with the ZC994/ZC995 adapter to form the plasmid pSW197 (FIG. 7).

The TPI1 promoter was inserted into plasmid pSW197 to construct pSW207. Plasmid pZV134 (Example 2) was digested with Bgl II and Eco RI to isolate the 0.9 kb promoter fragment. The TPI1 promoter fragment and the ZC994/ZC995 adapter, described above, were ligated in a three-part ligation with pUC18 that had been linearized by digestion with Sph I and Eco RI. The resultant plasmid, pSW198, was digested with Not I and Bam HI to isolate the 0.9 kb TPI1 promoter fragment. This fragment was ligated with pSW197 which had been linearized by digestion with Not I and Bam HI. The resultant plasmid was designated pSW207 (FIG. 7).

Example 7: Construction of Expression Vector pSW210

Figure 8:
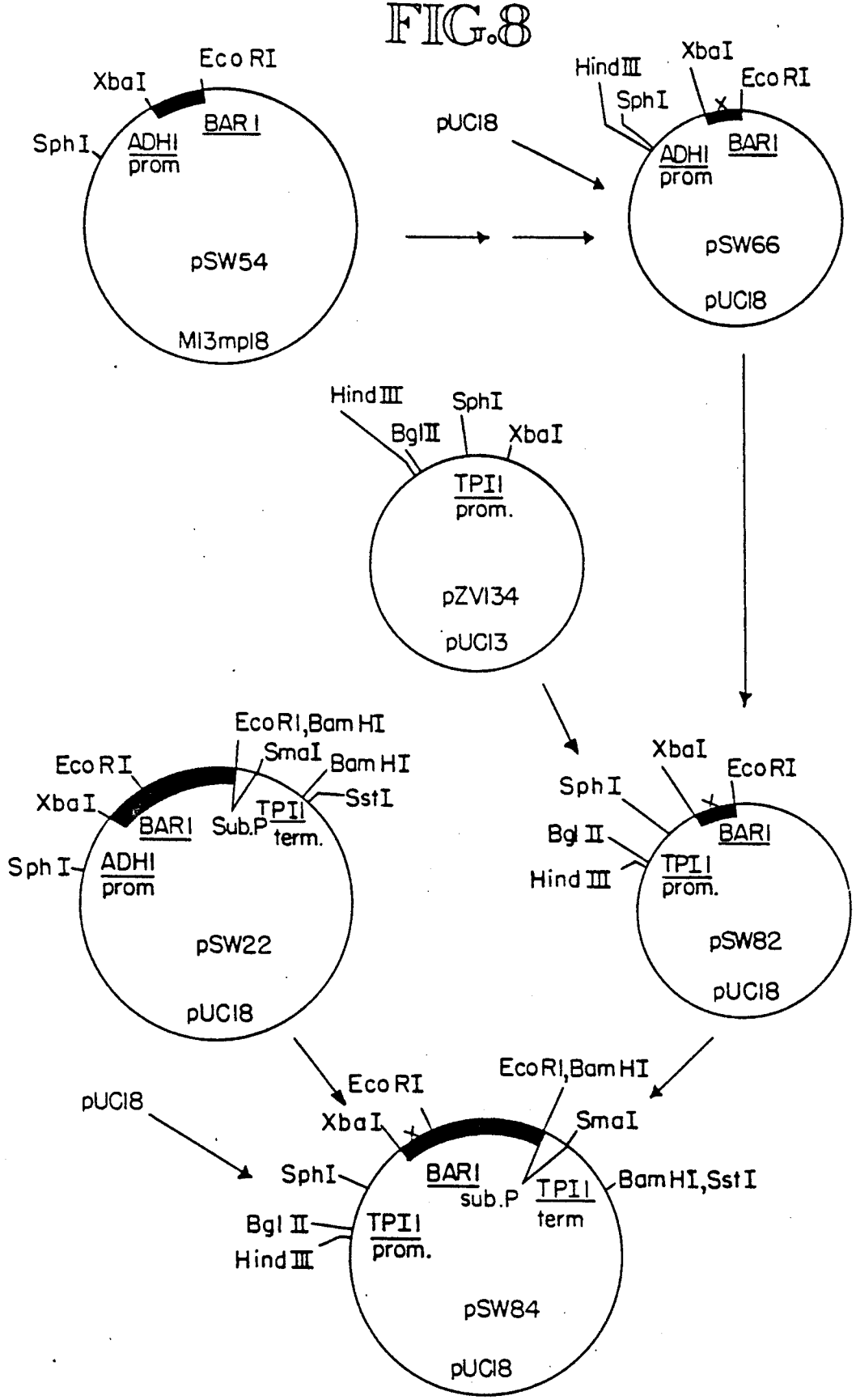
FIG. 8 illustrates the construction of plasmid pSW84.
Figure 9:
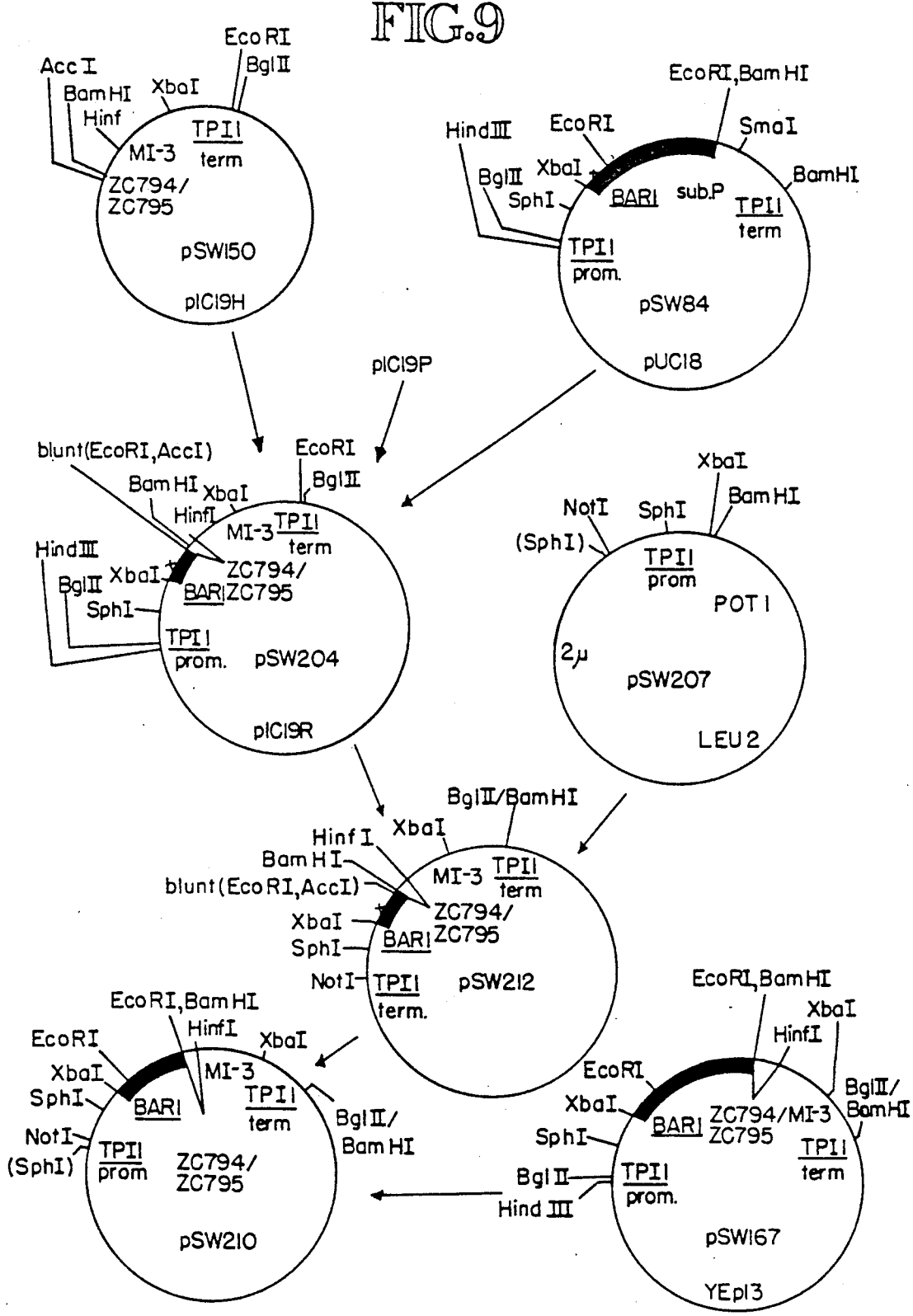
FIG. 9 illustrates the construction of expression vector pSW210.

An expression vector containing the sequence encoding the first 526 amino acids of Barrier fused to the MI-3 coding sequence was constructed as shown in FIGS. 8 and 9.

For ease of manipulation, a fragment comprising the ZC794/ZC795 adapter, the MI-3 coding sequence, and the TPI1 terminator was subcloned into pIC19H. Plasmid pSW127 (Example 4) was digested with Eco RI to isolate the 1.2 kb fragment comprising the 3' portion of BAR1, the ZC794/ZC795 adapter, the MI-3 coding sequence, and the TPI1 terminator. This 1.2 kb fragment was digested with Xho II to isolate the 0.96 kb fragment comprising the ZC794/ZC795 adapter, the MI-3 coding sequence, and the TPI1 terminator. This fragment was ligated with pIC19H which had been linearized by digestion with Bam HI and Eco RI. The resultant plasmid was designated pSW150 (illustrated in FIG. 9).

The TPI1 promoter fragment was obtained from plasmid pSW84. Plasmid pSW84 contains the TPI1 promoter, a mutated BAR1 gene fused to the substance P sequence and the TPI1 terminator, and was constructed as shown in FIG. 8. A 0.54 kb Sph I-Eco RI fragment comprising the ADH1 promoter and the first 119 bp of BAR1, derived from plasmid pSW22 (Example 4), was ligated into M13mp18 which had been linearized by digestion with Sph I and Eco RI. The resultant phage, designated pSW54, was subjected to in vitro mutagenesis (Zoller and Smith, ibid.) using the mutagenic oligonucleotide ZC634 (5'ATT ACT GCT CCT ACA AAC GAT3'). This mutation changed the leucine codon at position 25 to a proline codon to generate a signal peptide cleavage site mutant. Positive clones were sequenced to confirm the mutation, and a positive clone was designated mZC634-7. Replicative form DNA of mZC634-7 was digested with Sph I and Eco I to isolate the 0.54 kb fragment. This fragment was ligated into pUC18 which had been linearized by digestion with Sph I and Eco RI. The resultant plasmid, pSW66, was digested with Hind III and Xba I to remove the ADH1 promoter fragment. The 2.8 kb fragment containing the mutagenized BAR1 fragment and pUC18 was ligated to a Hind III-Xba I fragment from plasmid pZV134 (Example 2) comprising the TPI1 promoter. The resultant plasmid was designated pSW82. Plasmid pSW82 was digested with Hind III and Eco RI to isolate the 1.02 kb fragment comprising the TPI1 promoter and the mutagenized BAR1 fragment. Plasmid pSW22 was subjected to partial digestion with Eco RI and complete digestion with Sst I to isolate the 2.16 kb fragment comprising the C-terminal portion of the BAR1 gene fused to the substance P sequence and the TPI1 terminator. These two fragments were ligated in a three-part ligation with pUC18 which had been linearized by digestion with Hind III and Sst I. The resultant plasmid, pSW84, comprises the TPI1 promoter, the mutagenized BAR1 gene, and the TPI1 terminator.

For ease of manipulation, the TPI1 promoter-BAR1 fragment from pSW84 was ligated with the MI-3-TPI1 terminator fragment of pSW150 in the vector pIC19R (Marsh et al., ibid.). As shown in FIG. 9, plasmid pSW150 was linearized by digestion with Acc I, and the adhesive ends were blunted with DNA polymerase (Klenow fragment). The blunted fragment was then cut with Bgl II to isolate the 0.97 kb fragment comprising the ZC994/ZC995 adapter, the MI-3 coding sequence, and the TPI1 terminator. Plasmid pSW84 was digested with Eco RI, and the adhesive ends were blunted with DNA polymerase I (Klenow fragment). The blunted fragment was then cut with Hind III to isolate the 1.02 kb TPI1 promoter-BAR1 fragment. The 0.97 kb fragment from pSW150 and the 1.02 kb fragment from pSW84 were joined, in a three-part ligation, with PIC19R which had been linearized by digestion with Hind III and Bgl II. The resultant plasmid was designated pSW204.

The expression unit in pSW204 was put into pSW207 (Example 6) to make plasmid pSW212. Plasmid pSW204 was cut with Sph I and Bgl II to isolate the 1.3 kb expression unit. Plasmid pSW207 was cut with Sph I and Bam HI to isolate the partial TPI1 promoter-vector fragment. These two fragments were ligated together to make plasmid pSW212 (FIG. 9).

The full-length BAR1-MI-3 fusion was constructed by replacing the BAR1 fragment present in pSW212 with the BAR1 fragment from pSW167 (Example 4). Plasmid pSW212 was digested with Sph I and Bam HI to isolate the vector fragment containing the partial TPI1 promoter, the ZC794/ZC795 adapter, the MI-3 coding sequence, and the TPI1 terminator. Plasmid pSW167 was digested with Sph I and Bam HI to isolate the 1.81 kb partial TPI1 promoter and BAR1 sequences. This fragment was ligated with the pSW212 vector fragment to produce the expression vector pSW210 (FIG. 9).

Example 8: Construction of Expression Vector pSW219

Figure 10:
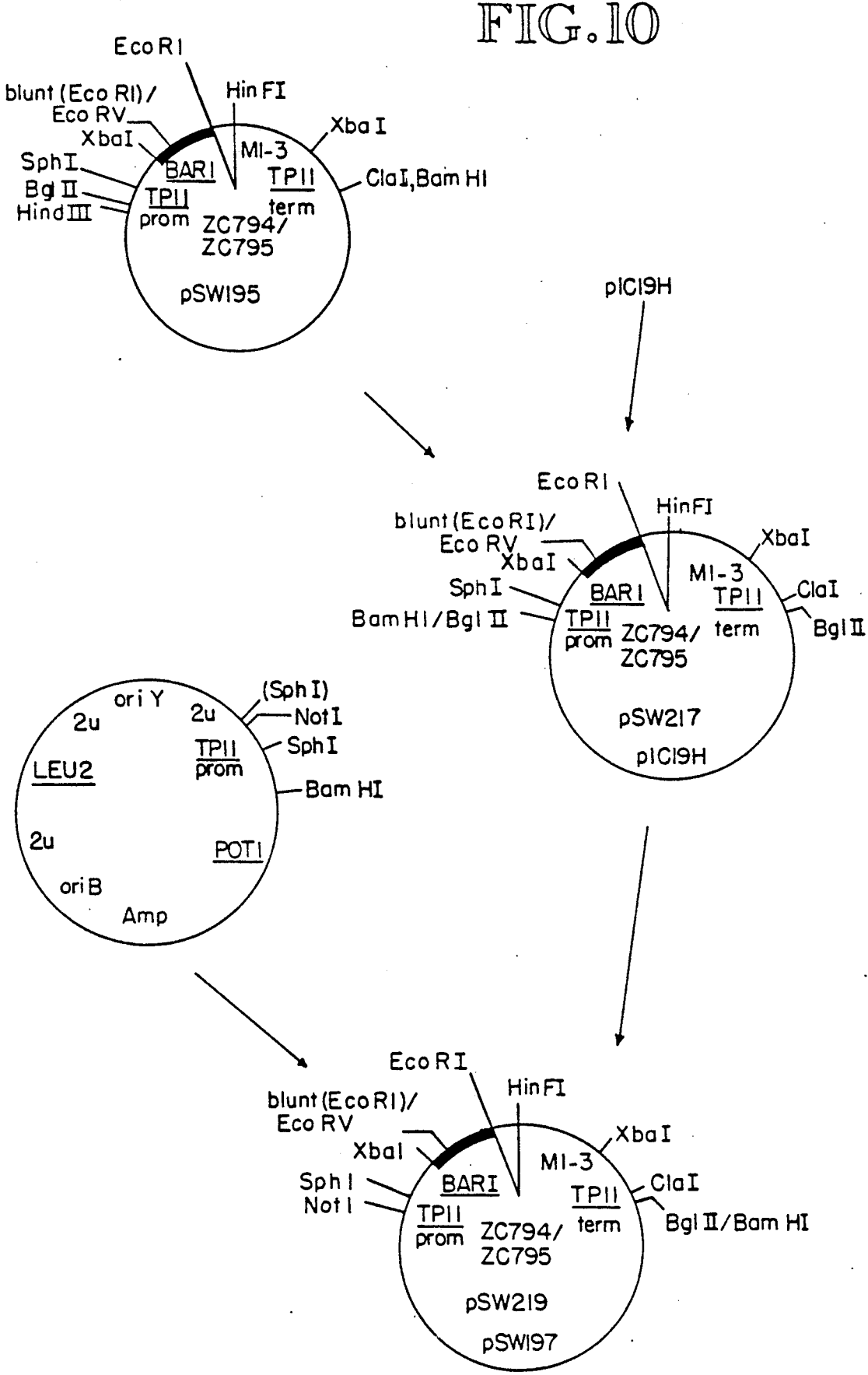
FIG. 10 illustrates the construction of expression vector pSW219.

Plasmid pSW219, comprising the expression unit present in pSW200 (Example 5) and the POT1 selectable marker, was constructed as follows (FIG. 10). Plasmid pSW195 (Example 5) was digested with Bgl II and Cla I to isolate the 2.4 kb fragment comprising the TPI1 promoter, the BAR1 signal sequence, the BAR third domain coding sequence, the MI-3 sequence, and the TPI1 terminator. This fragment was ligated with Bam HI-Cla I-linear zed pIC19H. The resultant plasmid, pSW217, contained the expression unit from pSW195 with a Bgl II site at the 3' end of the TPI1 terminator. Plasmid pSW217 was digested with Sph I and Bgl II to isolate the 1.7 kb fragment comprising the partial TPI1 promoter, the BAR1 signal and third domain sequences, the MI-3 coding sequence, and the TPI1 terminator. Plasmid pSW207 (Example 6) was digested with Sph I and Bam HI to isolate the partial TPI1 promoter-vector fragment. This fragment was ligated with the 1.7 kb fragment from pSW217 to produce the expression vector pSW219.

Example 9: Construction of Expression Vector pZV187

An alternative processing site to the dibasic cleavage site is the thrombin cleavage site. To construct the alternative expression unit, plasmid pSW195 was modified by in vitro mutagenesis to replace the Lys-Arg cleavage site with a thrombin cleavage site. This modification resulted in codons encoding the amino acids proline and arginine in place of those codons associated with the dibasic processing site. The resultant MI-3 expression vector, comprising the BAR1 signal sequence and third domain coding sequence, was designated pZV187.

Figure 11:
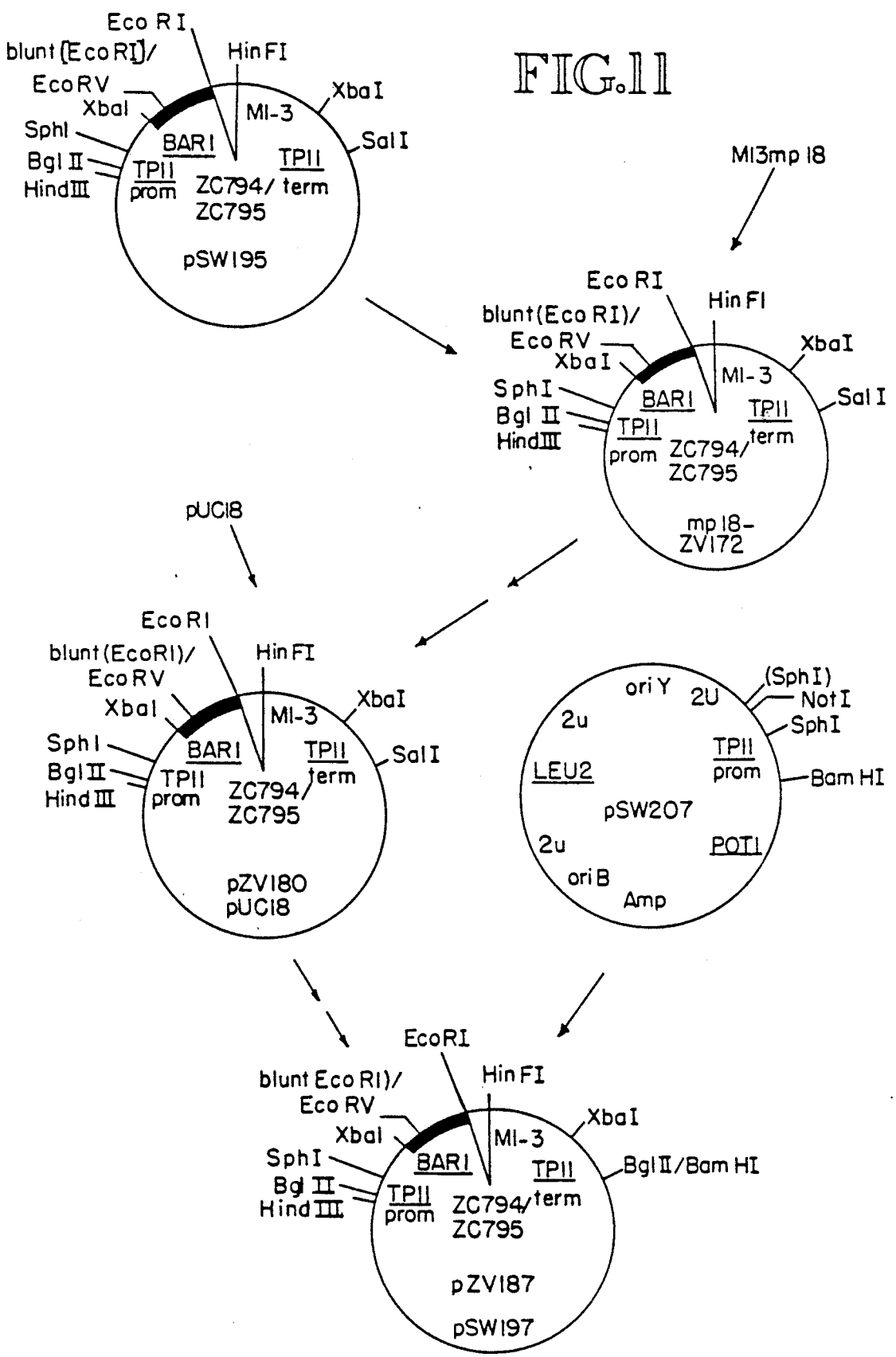
FIG. 11 illustrates the construction of expression vector pZV187.

FIG. 11 illustrates the construction of pZV187. Plasmid pSW195 was digested with Sph I and Sal I to isolate the 1.7 kb fragment comprising the BAR1-MI-3 fusion and the TPI1 terminator. This fragment was ligated with M13mp18 which had been previously digested to completion with Sph I and Sal I. The resultant phage clone was designated mp18-ZV172. Oligonucleotide ZC1083 (5'TCC TTG GAT CCA AGA TTC GTT³') was used to mutagenize mp18-ZV172 using the uracil method (Kunkel, *Proc. Natl. Acad. Sci. USA* 82:488-492, 1985). The resultant mutants were sequenced to confirm the mutagenesis and a positive clone was designated ZV172/1083. For convenience, the insert present in ZV172/1083 was subcloned into pUC18. The 1.7 kb Sph I-Sal I insert from ZV172/1083 was isolated and ligated with pUC18 which had been previously digested to completion with Sph I and Sal I. The resultant plasmid, pZV180, was digested to completion with Sal I. The adhesive ends of the linearized pZV180 were blunted using DNA polymerase I (Klenow fragment) and ligated to kinased Bgl II linkers. Excess linkers were removed by digestion with Bgl II. The linkered DNA was then cut to completion with Sph I to isolate the 1.7 kb insert. The 1.7 kb insert, comprising the partial TPI1 promoter, the BAR-MI-3 fusion and the TPI1 terminator, was ligated into the Sph I-Bam HI partial TPI1 promoter-vector fragment of plasmid pSW207 to construct pZV187.

Example 10: Transformation of Host Cells and Expression of the Insulin Analog MI-3

The expression vectors pSW167 and pSW200, comprising expression units in the vector YEp13; and expression vectors pSW210, pSW219 and pZV187, comprising expression units in the vector pSW197, were transformed into suitable yeast hosts by standard methods. The *S. cerevisiae* host strains contained mutations which were complemented by the selectable markers present on the plasmids.

Plasmid pSW167, comprising the coding sequence for the first 526 amino acids of the coding region of BAR1 fused to the coding sequence for MI-3 in YEp13, and plasmid pSW200, comprising the coding sequences for the BAR1 signal peptide and the BAR1 third domain fused to the coding sequence for MI-3 in YEp13, were transformed into *S. cerevisiae* strain ZA521 (MATa leu2-3 leu2-112 ura3 pep4::URA3 bar1 gal2).

Transformants were selected for their ability to grow on synthetic growth media lacking leucine.

Transformants were grown overnight at 30° C. in 5 ml −LeuD (Wickerham, L. J., *J. Bact.* 52 293-301, 1946; containing Difco Yeast Nitrogen Base as the nitrogen source). The transformants were diluted 1:100 into 20 or 50 ml −LeuD and grown at 30° C. for 24 or 48 hrs. The cells were pelleted and washed before freezing at −70° C. The spent media were spun twice and decanted away from the cell material before being frozen at −70° C. The MI-3 levels, determined by radioimmunoassay (RIA, see Example 14), showed pSW167 transformants to produce 38 pg/ml MI-3 immunoreactive material and pSW200 transformants to produce 113 pg/ml MI-3 immunoreactive material at 54 hours.

Plasmid pSW210, comprising the sequence encoding the first 526 amino acids of BAR1 fused to the coding sequence for MI-3 in pSW197, and plasmid pSW219, comprising the coding sequences for the BAR1 signal peptide and the BAR1 third domain fused to the coding sequence for MI-3 in pSW197, were transformed into *S. cerevisiae* strains GA18-1C (MATa leu2-3 leu2-112 ura3 Δtpi1::LEU2 [cir° ]) and ZM114 (MATa leu2-3,112 ura3-52 ade2-101 pep4::TPI promoter-CAT Δtpi1::URA3 vpt3 suc2-Δ9 [cir° ]). Transformants were selected for their ability to grow in the presence of glucose.

The expression and secretion of MI-3 from strain GA18-1C transformed with plasmids pSW210 and pSW219 were achieved by first growing transformants overnight at 30° C. in 5 ml MED 1 (2% Bacto Yeast Extract, 0.5% ammonium sulfate, 6% glucose). The transformants were diluted 1:100 into 20 or 50 ml MED 1 and grown at 30° C. for 24 or 48 hrs. The cells were pelleted, washed, and frozen at −70° C. The spent media were spun twice and decanted away from the cell material, then frozen at −70° C. The MI-3 levels, determined by RIA, showed pSW210 transformants to produce 0.3 μg/ml MI-3 immunoreactive material and pSW219 transformants to produce 0.15 μg/ml MI-3 immunoreactive material at 24 hrs.

The level of expression and secretion of MI-3 from pSW219 transformants of strain ZM114 was also measured by high-pressure liquid chromatography (HPLC) assay. Transformants were grown overnight at 30° C. in 5 ml supplemented YEPD (YEPD+40 mg/L Ade+80 mg/L Leu+10 mM CaCl₂, adjusted to 6% glucose). The overnight culture was diluted 1:100 in 50 ml of supplemented YEPD and grown at 30° C. Duplicate 4 ml samples were taken at 30, 48 and 75 hrs. Samples were centrifuged and the supernatants were saved. 0.5 ml aliquots of the supernatants were mixed with 0.5 ml fermentation broth (552 g 96% EtOH+349 g H₂O+5 ml conc. H₂SO₄) and allowed to incubate at room temperature for 30 min. The mixtures were then filtered through 0.2 μm Acrodiscs (Gelman Sciences, Ann Arbor, Mich.) and frozen at −20° C. The MI-3 levels, as determined by HPLC assay (Example 14B), showed the pSW219 transformants to produce 14 μg/ml MI-3 at 75 hrs.

Plasmid pZV187, containing a thrombin cleavage site between the BAR1 third domain and the MI-3 coding sequence, was transformed into *S. cerevisiae* strains GA18-1C and ZM114. Transformants were selected for their ability to grow in the presence of glucose. Transformants were grown overnight in 5 ml YEP+6% glucose (1% Bacto Yeast Extract, 2% Bacto Yeast Peptone, with 6% dextrose added after autoclaving). The overnight cultures were diluted 1:100 into 10 ml YEP+6% glucose and grown at 30° C. Samples were taken at 26 hrs and 48 hrs. Samples were centrifuged to pellet the cells, and the supernatants were decanted and frozen at −70° C. The MI-3 levels were determined by radioimmunoassay. GA18-1C transformants were shown to produce 0.9 ng/ml MI-3 immunoreactive material at 48 hrs. ZM114 transformants were shown to produce 0.52 ng/ml MI-3 immunoreactive material at 48 hrs.

Example 11: Construction of Expression Vectors pSW290 and pSW281

A construction comprising the TPI1 promoter, the BAR1 signal sequence, the BAR1 third domain sequence with a glycosylation site mutation at position #7, the MI-3 coding sequence, the TPI1 terminator and pDPOT vector sequences was assembled from pZC891, which was constructed as follows. The Sph I-Bam HI fragment of pSW195 (Example 5), comprising a portion of the TPI1 promoter, the BAR1 signal sequence and the BAR1 third domain, was cloned into M13mp18 which had been linearized by digestion with Sph I and Bam HI. Single-stranded template DNA prepared from the resultant construct was subjected to in vitro mutagenesis using ZC891 (5' AGT CGA TGC TCT ACG 3') using essentially the method described by Zoller and Smith (ibid., 1983). Mutagenesis using ZC891 produced an Asn → Gln mutation at position #7 of the BAR1 third domain. A positive c)one, identified by plaque hybridization and confirmed by dideoxy sequencing, was designated pZC891.

Replicative form pZC891 DNA was prepared and digested with Sph I and Bam HI to isolate the 0.73 kb fragment comprising a portion of the TPI1 promoter, the BAR1 signal sequence, and BAR1 third domain containing the ZC891 mutation at glycosylation site #7. Plasmid pSW210 (Example 7) was digested with Sph I and Bam HI to isolate the 12.3 kb fragment comprising the 5' 0.7 kb of the TPI1 promoter, the MI-3 coding sequence, the TPI1 terminator and pDPOT vector sequences. The pSW210 fragment was joined with the pZC891 fragment by ligation to generate plasmid pSW290.

A construct comprising the TPI1 promoter, the BAR1 signal sequence, the BAR1 third domain sequence with a glycosylation site mutation at position #8, the MI-3 coding sequence, the TPI1 terminator and pDPOT vector sequences was assembled in a manner analogous to the construction of pSW290. Site-directed in vitro mutagenesis on single-stranded template DNA of pSW253 using ZC1330 (5'AAA CCT CTC AAG AAA CCA A 3') and the method described by Zoller and Smith (ibid., 1983) produced a mutation which resulted in an Asn → Gln substitution at glycosylation site #8. A positive clone was identified and was digested with Sph I and Bam HI to isolated the 0.73 kb fragment containing the ZC1330 mutation. The 0.73 kb fragment was then joined with the 12.3 kb Sph I-Bam HI fragment of plasmid pSW210. The resultant plasmid was designated pSW281.

Example 12: Transformation of Host Cells and Expression of the Insulin Precursor MI-3 from Plasmid pSW290

The expression of the insulin precursor MI-3 from plasmid pSW290 was compared to the vector pDPOT and analogous constructs pIN4A, which comprised the TPI1 promoter, MFα1 signal sequence, the MI-3 coding sequence, the TPI1 terminator and pDPOT vector sequences, and pSW219 (Example 8), which comprised the TPI1 promoter, the BAR1 signal sequence, the wild-type BAR1 third domain sequence, the MI-3 coding sequence, the TPI1 terminator and pDPOT vector sequences. Expression was analyzed in growth curve experiments. Plasmids pSW290, pDPOT, pIN4A and pSW219 were transformed into *S. cerevisiae* strain ZM114 (Example 10) by standard methods. Five ml YEPD+ade+leu (1% yeast extract, 2% peptone, 2% glucose, 40 mg/l adenine, 80 mg/l leucine) overnight starter cultures were grown for each transformant. The starter cultures were diluted to an $OD_{600}$ of 0.1 in 60 ml YEPD+ade+leu and were grown at 30° C. with aeration. Samples were taken at 22, 34.5, 46.5 and 57.2 hours after inoculation.

At each time point, the $OD_{600}$ was determined and 5 ml samples were taken from each culture. The ZM114[SW290] culture was found to exhibit no growth lag as has been found with the analogous construct, pSW219, which encodes wild-type glycosylation in the BAR1 third domain (Table 1). The cells were removed by centrifugation at 4° C. and the supernatants were saved. Two 0.5 ml aliquots of each supernatant sample were dispensed into two microfuge tubes. The 0.5 ml aliquots were prepared for HPLC analysis by dilution with 0.5 ml fermentation broth followed by incubation for 30 min at room temperature, centrifugation for 5 min in an Eppendorf microfuge (Brinkmann, Westbury, N.Y.) at 4° C., and filtration through a 0.45 um filter into a fresh microfuge tube. Samples were stored at −70° C. prior to assay. High-pressure liquid chromatography assays were carried out on the culture supernatants as described in Example 16.B. The results of the assays (Table 2) showed that ZM114[pSW290] exhibited higher secretion of MI-3 than the analogous construct, pIN4A, transformed into ZM114.

TABLE 1

| Hours | Transformant: | | | |
|---|---|---|---|---|
| | pDPOT | pIN4A | pSW219 | pSW290 |
| 22 | 15.6 | 11.8 | 0.98 | 14.1 |
| 34.5 | 17.0 | 15.0 | 3.8 | 16.4 |
| 46.5 | 18.6 | 17.6 | 8.6 | 16.6 |
| 57.2 | 18.2 | 21.0 | 10.2 | 19.5 |

TABLE 2

| Concentration of MI-3 (mg/L) as determined by HPLC assay | | | | |
|---|---|---|---|---|
| | Transformant: | | | |
| Hours | pDPOT | pIN4A | pSW219 | pSW290 |
| 22 | 0 | 17.7 | 2.31 | 29.4 |
| 34.5 | 0 | 20.7 | 8.42 | 31.8 |
| 46.5 | 0 | 31.7 | 34.2 | 37.6 |
| 57.2 | 0 | 35.1 | 42.7 | 50.2 |

Figure 12:
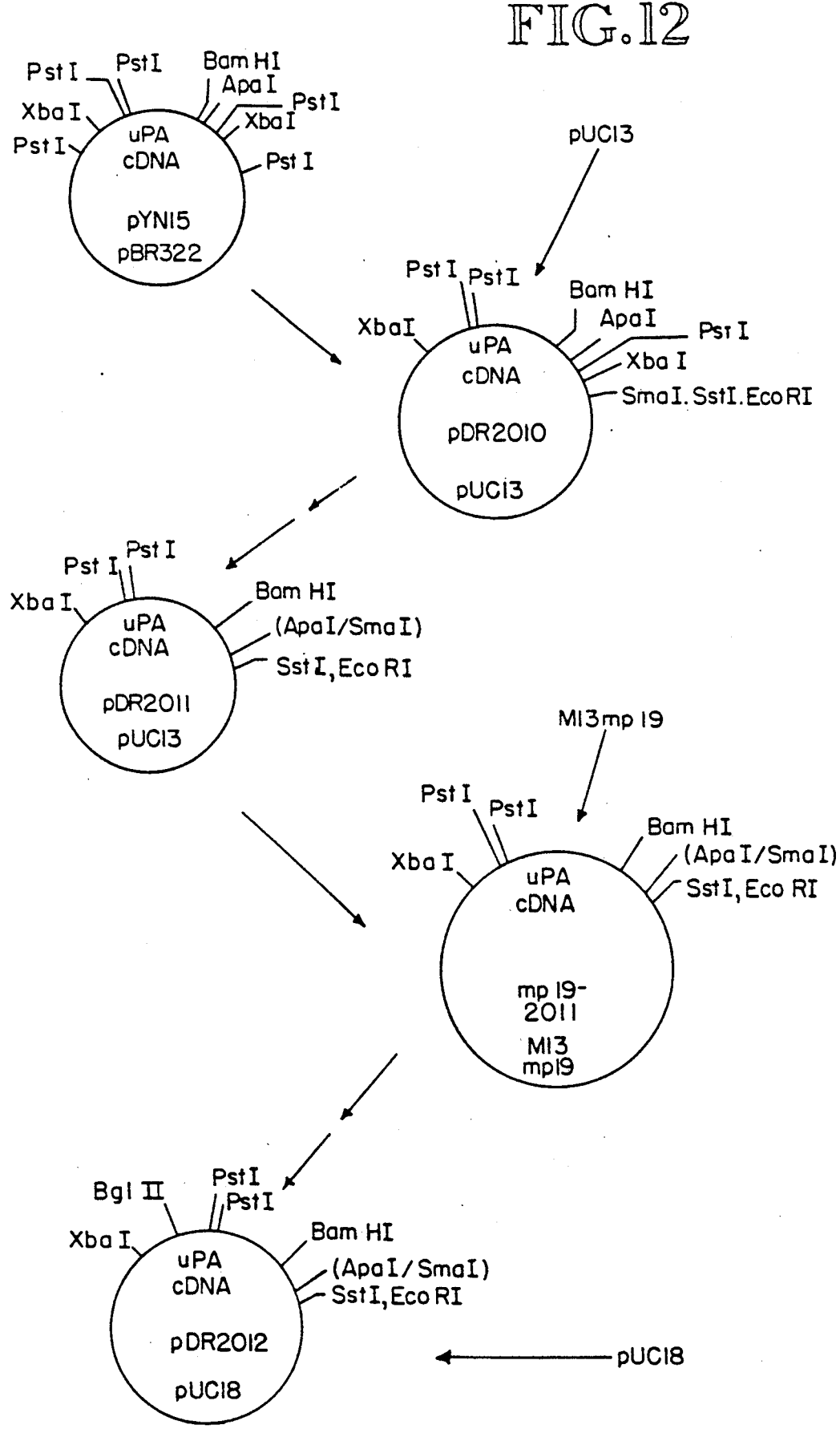
FIG. 12 illustrates the construction of plasmid pDR2012.

Example 13: Hybrid Secretory Peptide Comprising the PHO5 Signal Peptide and the BAR1 Third Domain Sequence An expression unit comprising the PHO5 signal peptide, the BAR1 third domain sequence, and a porcine urokinase (uPA) cDNA was constructed and placed into the vector YEp13. The uPA cDNA was derived from plasmid pYN15 (Nagamine et al., *Nuc. Acids Res.* 12:9525-9541, 1984), comprising the uPA cDNA as a 2.3 kb insert in the vector pBR322 (FIG. 12). The cDNA sequence was first altered to place an Xba I site 3' to the uPA stop codon. Plasmid pYN15 was cut with Xba I to isolate the 1.9 kb fragment containing the uPA coding sequence. The fragment was ligated into pUC13 which had been digested to completion with Xba I. The ligation mixture was transformed into *E. coli* strain JM83. Plasmid DNA was prepared from the transformants, and a plasmid with the insert in the correct orientation was designated pDR2010. Plasmid pDR2010 was linearized by digestion with Apa 1, and the adhesive ends were blunted with T4 DNA polymerase. The blunted fragment was cut with Sma I to remove the 585 bp 3' non-coding region, and was re ligated, resulting in plasmid pDR2011.

The cDNA fragment present in pDR2011 was then altered to place a Bgl II site 5' to the first amino acid codon of uPA. Plasmid pDR2011 was cut with Xba I and Eco RI to isolate the 1.35 kb uPA fragment, which was then ligated with M13mp19 which had been digested to completion with Xba I and Eco RI. The resultant phage clone was designated M13mp19-2011. Oligonucleotide ZC558 (5'AGT TCA TGA GAT CTT TTG GAG T3') was designed to create a Bgl II site at the first amino acid of uPA. Plasmid M13mp19-2011 was subjected to in vitro mutagenesis by the two-primer method of Zoller and Smith (1984, ibid.) using ZC558 as the first primer and ZC87 (5'TCC CAG TCA CGA CGT3') as the second primer. Positive clones, identified by hybridization to kinased ZC558, were cut with Bgl II and Eco RI to confirm the introduction of a Bgl II site. The resultant phage, mp19-2011-558, was digested with Xba I and Sst I to isolate the 1.35 kb fragment comprising the mutagenized uPA sequence. This fragment was joined to pUC18 which had been linearized by digestion with Xba I and Sst I. The resultant plasmid was designated pDR2012 (FIG. 12).

The uPA cDNA present in plasmid pDR2012 was modified to add an XbaI site 3' to the stop codon. Plasmid pDR2012 was linearized by digestion with Eco RI and the adhesive ends were blunted by treatment with DNA Polymerase I (Klenow Fragment). The blunt-ended fragment was ligated to kinased XbaI linkers (CTCTAGAG) and transformed into *E. coli* strain JM83. Plasmid DNA isolated from the transformants was analyzed by digestion with Bgl II and Xba I. Positive clones were designated pZV112 (FIG. 13).

Figure 13:
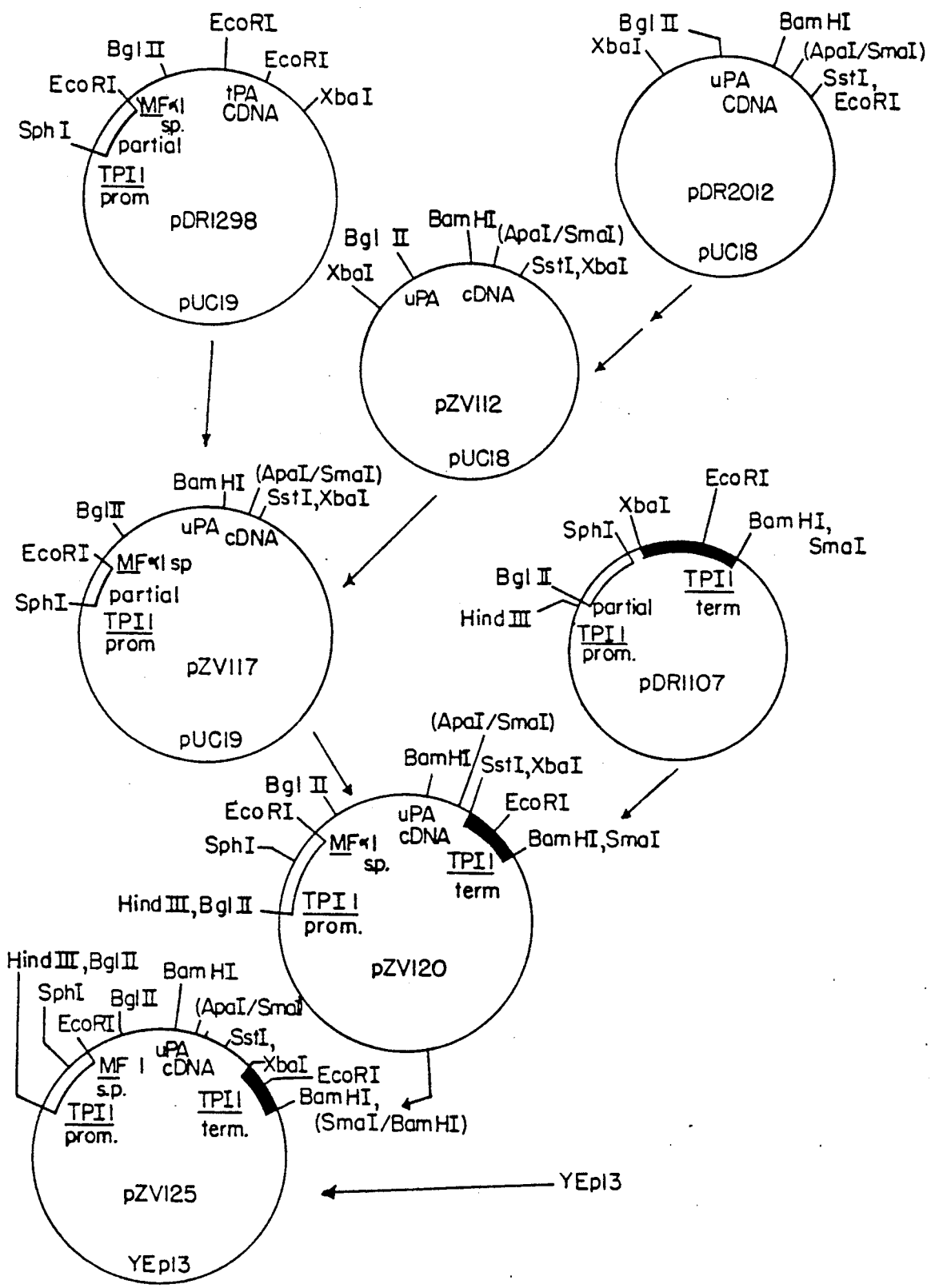
FIG. 13 illustrates the construction of plasmid pZV125.
Figure 14:
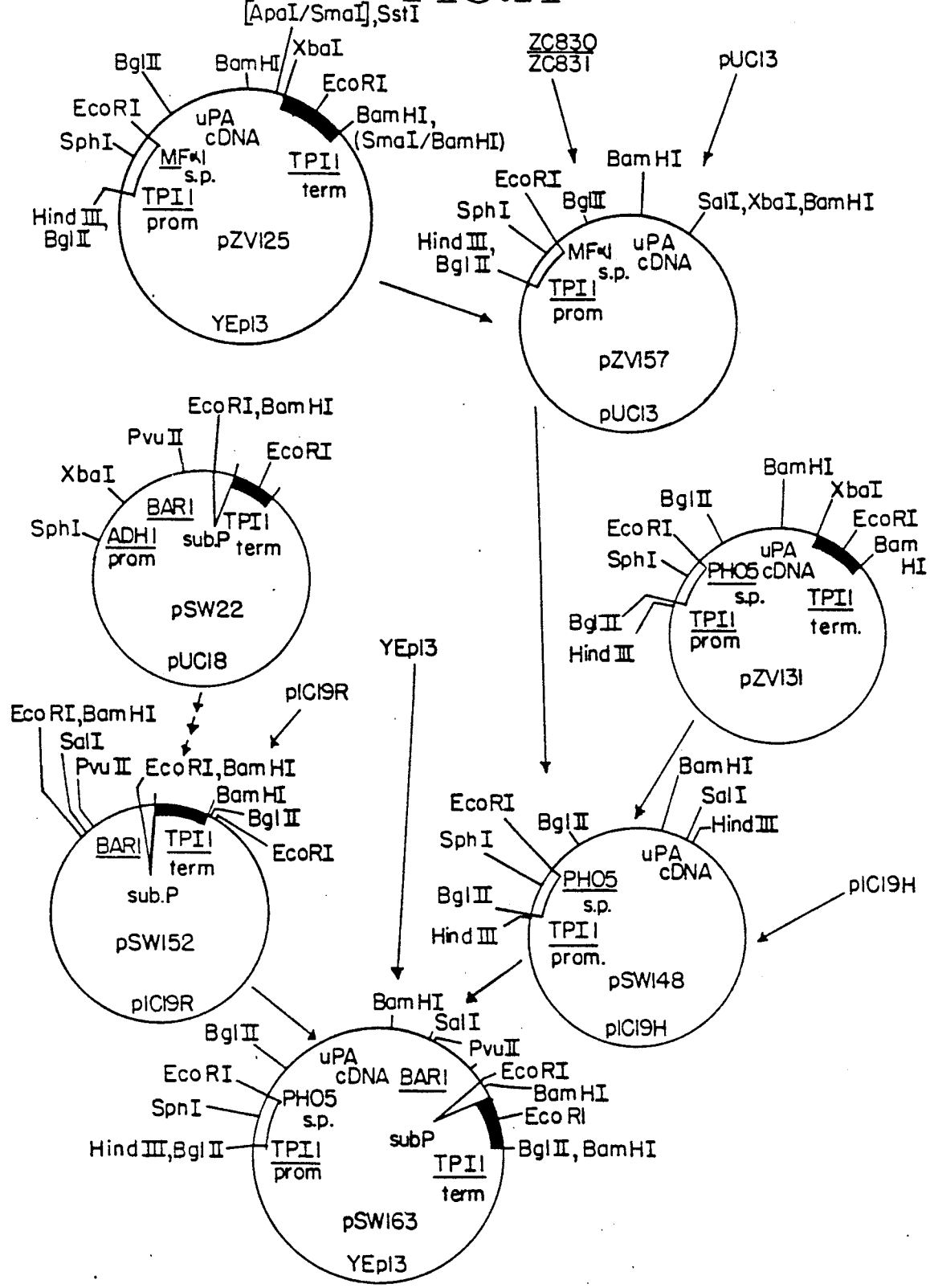
FIG. 14 illustrates the construction of plasmid pSW163.

The uPA cDNA present in plasmid pZV112 was substituted for the tissue plasminogen activator (tPA) cDNA sequence in plasmid pDR1298, which contains the partial TPI1 promoter, the MFα1 pre-pro sequence, and a tPA cDNA (FIG. 13). Plasmid pDR1298 was digested with Bgl II and Xba I to isolate the 3.25 kb fragment comprising the TPI1 promoter, the MFα1 signal sequence, and the pUC18 vector. Plasmid pZV112 was digested with Bgl II and Xba I to isolate the uPA cDNA. This fragment was ligated with the 3.25 kb pDR1298 fragment. The resultant plasmid, pZV117, was digested with Sph I and Xba I to isolate the partial TPI1 promoter, MFα1 signal sequence, and the uPA cDNA. Plasmid pDR1107 (Example 2) was digested with Sph I and Xba I to isolate the 3.6 kb fragment comprising the partial TPI1 promoter, TPI1 terminator, and the pUC13 vector. This fragment was then ligated to the 3.25 kb pZV117 fragment, resulting in plasmid pZV120. Plasmid pZV120 was digested with Hind III and Sma I to isolate the expression unit. Plasmid YEp13 was digested with Bam HI and blunt-ended with DNA polymerase I (Klenow fragment). The blunt-ended fragment was then cut with Hind III to isolate the vector portion, which was then ligated with the expression unit of pZV120 to make plasmid pZV125.

The uPA cDNA in plasmid pZV125 was modified to place a Sal I site 3' to the uPA cDNA stop codon, using a synthetic adapter. Plasmid pZV125 was digested with Hind III and Bam HI to isolate the 2.5 kb fragment comprising the TPI1 promoter, the MFα1 pre-pro sequence, and the partial uPA cDNA. Oligonucleotides ZC830 (5'TCG ACG TGA GCT AGC CCG TTT TCA CCA CCA ACG TGA GTG TG3') and ZC831 (5'GAT CCA CAC TCA CGT TGG TGG TGA AAA CGG GCT AGC TCA CG3') were kinased and annealed to create a yeast codon-optimized adapter encoding the terminal 13 amino acids of uPA, with Bam HI and Sal I adhesive ends. The ZC830/ZC831 adapter and the 2.5 kb fragment from pZV125 were joined in a three-part ligation with pUC13 which had been linearized by digestion with Hind III and Sal I. The resultant plasmid, designated pZV157, comprises the uPA cDNA with a Bgl II site 5' to the first codon of uPA and a Sal I site 3' to the uPA stop codon.

The uPA cDNA from pZV157 was joined to the TPI1 promoter and PHO5 signal peptide sequence to construct pSW148. Plasmid pZV157 was digested with Bgl II and Sal I to isolate the 1.3 kb uPA cDNA. A 0.96 kb Bgl II fragment comprising the TPI1 promoter-PHO5 signal peptide sequence, derived from plasmid pDR1394 [a pUC18-based plasmid containing the TPI1 promoter joined to a synthesized sequence encoding the yeast PHO5 (Arima et al., *Nuc. Acids Res.* 11:1657–1672, 1983) signal peptide], and the uPA cDNA fragment were joined in a three-part ligation with Bgl II-Sal I-cut pIC19H. The resultant plasmid was designated pSW148.

Plasmid pSW152, comprising the BAR1 third domain sequence fused to the substance P sequence and the TPI1 terminator, was constructed as follows. Plasmid pSW22 (Example 4 was digested with Pvu II to isolate the 1.16 kb BAR1-substance P fragment. Kinased and annealed Sal I linkers (5'CGT CGA CG3') were ligated to the 1.16 kb fragment. Excess linkers were removed by digestion with Sal I and Sst I. The 1.0 kb fragment was isolated and ligated to pIC19R which had been linearized with Sal I and Sst I. The resultant plasmid was designated pSW152.

Figure 15:
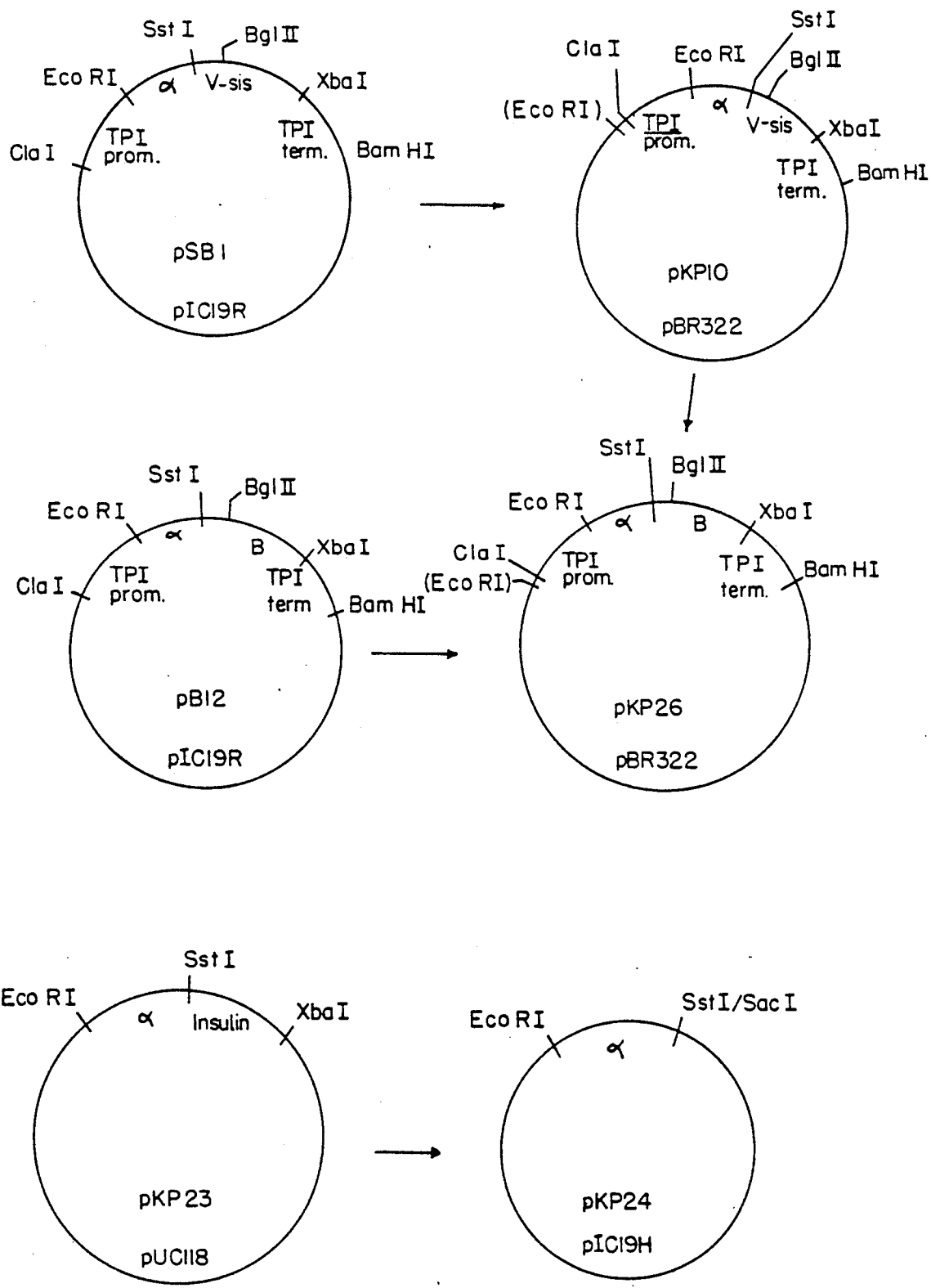
FIG. 15 illustrates the construction of the plasmids pKP24 and pKP26.

Plasmid pSW148 was digested with Hind III and Sal I to isolate the 2.2 kb fragment comprising the TPI1 promoter, the PHO5 signal sequence, and the uPA cDNA. Plasmid pSW152 was digested with Sal I and Bgl II to isolate the 1.1 kb fragment comprising the BAR1 third domain-substance P fusion and the TPI1 terminator. The 2.2 kb pSW148 fragment was joined to the 1.1 kb pSW152 fragment in a three-part ligation with Hind III-Bam HI-cut YEp13. The resultant plasmid was designated pSW163 (FIG. 15).

Example 14: Transformation of Host Cells and Expression of Urokinase

Plasmid pSW163, comprising the TPI1 promoter, the PHO5 signal sequence, the uPA cDNA, the BAR1 third domain, and the TPI1 terminator in the yeast vector YEp13, was transformed into yeast strains ZY100 (MATa ade2-101 leu2-3,112 ura3-52 suc2-Δ9 gal2 pep4::CAT) and ZY200 (MATa ade2-101 leu2-3,112 ura3-52 suc2-Δ9 gal2 pep4::CAT vpt3). Transformants were selected for their ability to grow on synthetic growth media lacking leucine.

The expression and secretion of porcine urokinase from pSW163 transformants were achieved by first growing transformants overnight at 30° C. in 5 ml −Leu6%D+0.1 M succinate pH 5.5 (−Leu containing 6% glucose and 0.1 M succinate, pH adjusted to pH 5.5 with NaOH prior to autoclaving). The overnight cultures were diluted 1:1000 in 5 ml −Leu6%D+0.1 M succinate pH 5.5 and grown for 37 hrs at 30° C. The cells were pelleted, and the supernatant was decanted and saved. UPA activity was measured by the fibrin lysis assay (Example 16C). Using this method, uPA was detected at levels of 7.2 μg/l in the cell extract and 38 μg/l in the supernatant from pSW163 transformants of ZY200.

Example 15: Expression and Secretion of PDGF BB Using the BAR1 Secretion Signal

A. Cloning of PDGF Sequences

Construction of a sequence encoding the B-chain of PDGF is disclosed by Murray et al. (U.S. Pat. Nos. 4,766,073 and 4,769,328, which are incorporated herein by reference). As described by Murray et al. (U.S. Pat. No. 4,766,073), the expression vector pB12 (FIG. 15) comprises a DNA sequence encoding human PDGF B-chain operatively linked to the *S. cerevisiae* TPI1 promoter, MFα1 pre-pro sequence and TPI1 terminator. Also as described in U.S. Pat. No. 4,766,073, the vector pSB1 (FIG. 15) comprises an expression unit consisting of the TPI1 promoter, MFα1 pre-pro sequence, v-sis coding sequence and TPI1 terminator.

The MFα1/B-chain sequence was substituted for the MFα1/v-sis sequence in the pSB1 vector. The pSB1 expression unit was inserted into a modified pBR322 plasmid lacking an Eco RI site. The resultant vector, designated pKP10 (FIG. 15), was digested with Eco RI and Xba I to remove the MFα1/v-sis fragment. The pB12 MFα1/B-chain fragment was then inserted into the pKP10 expression unit to construct pKP26 (FIG. 15).

A codon-optimized alpha-factor sequence was then introduced into the expression unit. An Eco RI-Xba I fragment comprising the alpha factor pre-pro and insulin sequences (Example 3) was cloned into Eco RI, Xba I digested pUC118 (Vieira and Messing, *Meth. Enzymology* 153:3–11, 1987) and single-stranded template DNA was prepared. This template was then mutagenized according to the two-primer method (Zoller and Smith, *DNA* 3:479–488, 1984) using the mutagenic oligonucleotide ZC862 (5'CGA ATC TTT TGA GCT CAG AAA CAC C 3'). The mutagenesis resulted in the creation of an Sst I site at the 3' end of the alpha-factor leader. A correctly altered plasmid was selected and designated pKP23. The leader sequence was excised from pKP23 by digestion with Eco RI and Sst I, and the leader fragment was subcloned into Eco RI+Sac I-cut pIC19H (Marsh et al., *Gene* 32:481–486, 1984). The resultant plasmid was designated pKP24 (FIG. 15). Plasmid pKP26 was cut with Eco RI and Sst I to remove the α-factor sequence. The codonoptimized α-factor sequence was then removed from pKP24 as an Eco RI-Sst I fragment and joined to the linearized pKP26. The resultant vector was designated pKP28 (FIG. 16).

The Sst I site introduced into the alpha-factor leader to facilitate vector construction was then removed to restore the wild-type coding sequence. Plasmid pKP28 was digested with Eco RI and Xba I and the alpha-factor--B-chain fusion sequence was recovered. This fragment was cloned into pUC118 and single-stranded template DNA was isolated. The template was mutagenized by the two primer method using the mutagenic oligonucleotide ZC1019 (5'ACC CAA GGA TCT CTT GTC CAA ACA AAC ACC TTC TTC 3'). A correctly mutagenized plasmid was designated pKP32.

Figure 16:
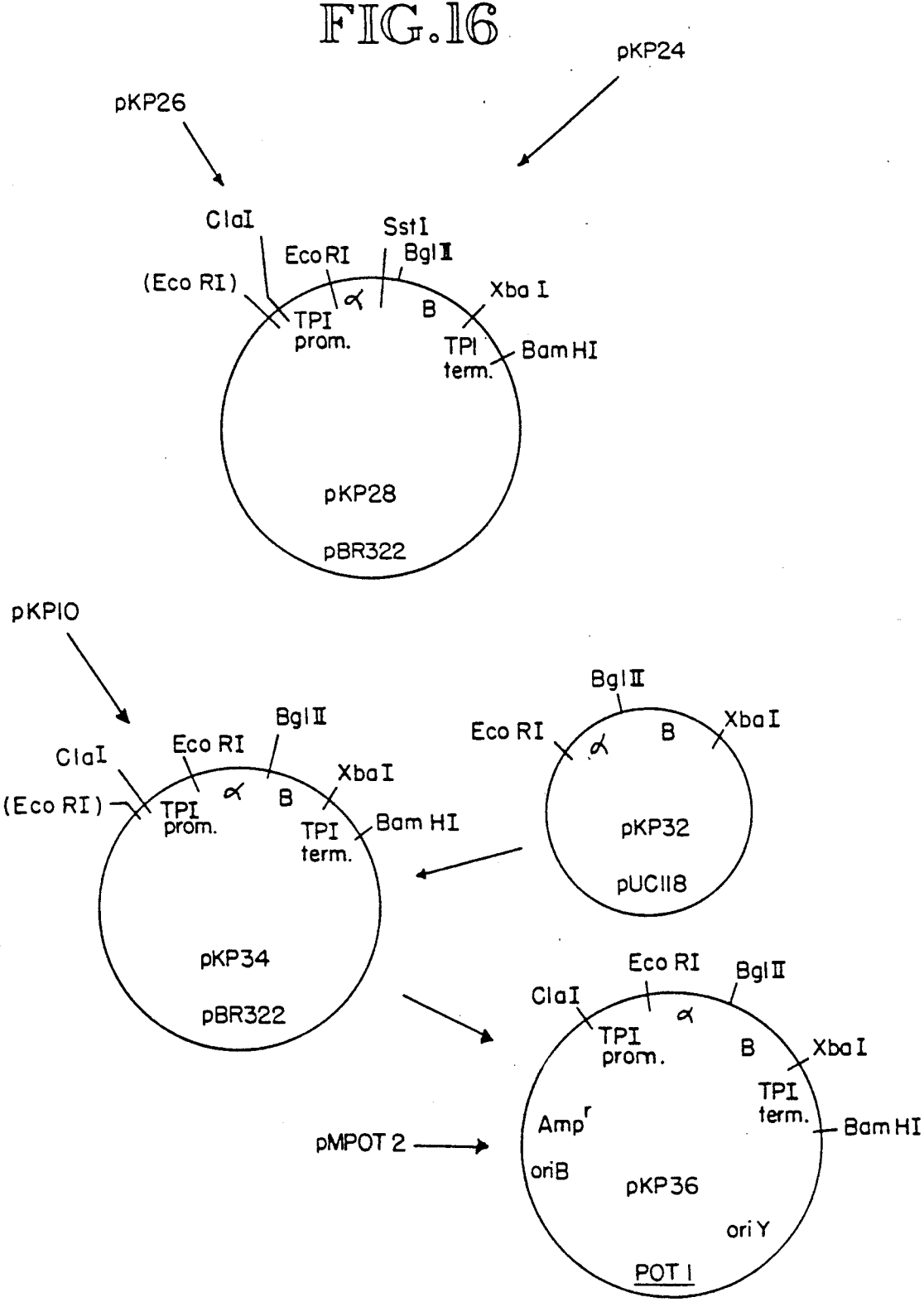
FIG. 16 illustrates the construction of plasmid pKP36.

The entire expression unit was then reconstructed as shown in FIG. 16. Plasmid pKP32 was digested with Eco RI and Xba I and the alpha-factor--B-chain fragment was recovered. This fragment was inserted into Eco RI, Xba I cut pKP10 to construct pKP34. Plasmid pKP34 was digested with Cla I and Bam HI and the expression unit was recovered. This fragment was inserted into Cla I, Bam HI digested pMPCT2 (a yeast 2 micron-based plasmid containing yeast and bacterial replication origins, ampicillin resistance gene and POT1 selectable marker, which has been deposited with American Type Culture Collection under accession number 67788) to construct pKP36.

The codon-optimized PDGF A-chain sequence from plasmid pA7 (Murray et al., U.S. Pat. No. 4,766,073) was combined with the codon-optimized alpha-factor leader sequence in a series of construction steps parallel to those described above for B-chain. The pA7 A-chain sequence was isolated as a Sst I-Xba I fragment and inserted into Sst I, Xba I-cut pKP28 to construct pKP27. Plasmid pKP27 was digested with Eco RI and Xba I and the alpha-factor--A-chain fragment was cloned into pUC118.

Mutagenesis, using the oligonucleotide ZC1018 (5'TTC GAT AGA TCT CTT GTC CAA AGA AAC ACC TTC TTC 3'), was carried out as described above to remove the Sst I site and restore the wild-type alpha-factor sequence. The corrected plasmid was designated pKP31.

A codon-optimized expression vector was then constructed. Plasmid pKP31 was digested with Eco RI and Xba I and the alpha-factor--A-chain fragment was joined to Eco RI, Xba I cut pKP10. The resultant vector, designated pKP33 (FIG. 17), contained the entire expression unit. Plasmid pKP33 was digested with Cla I and Bam HI and the expression unit fragment was recovered. This fragment was inserted into Cla I, Bam HI-cut pMPOT2 to construct the expression vector pKP35.

Figure 17:
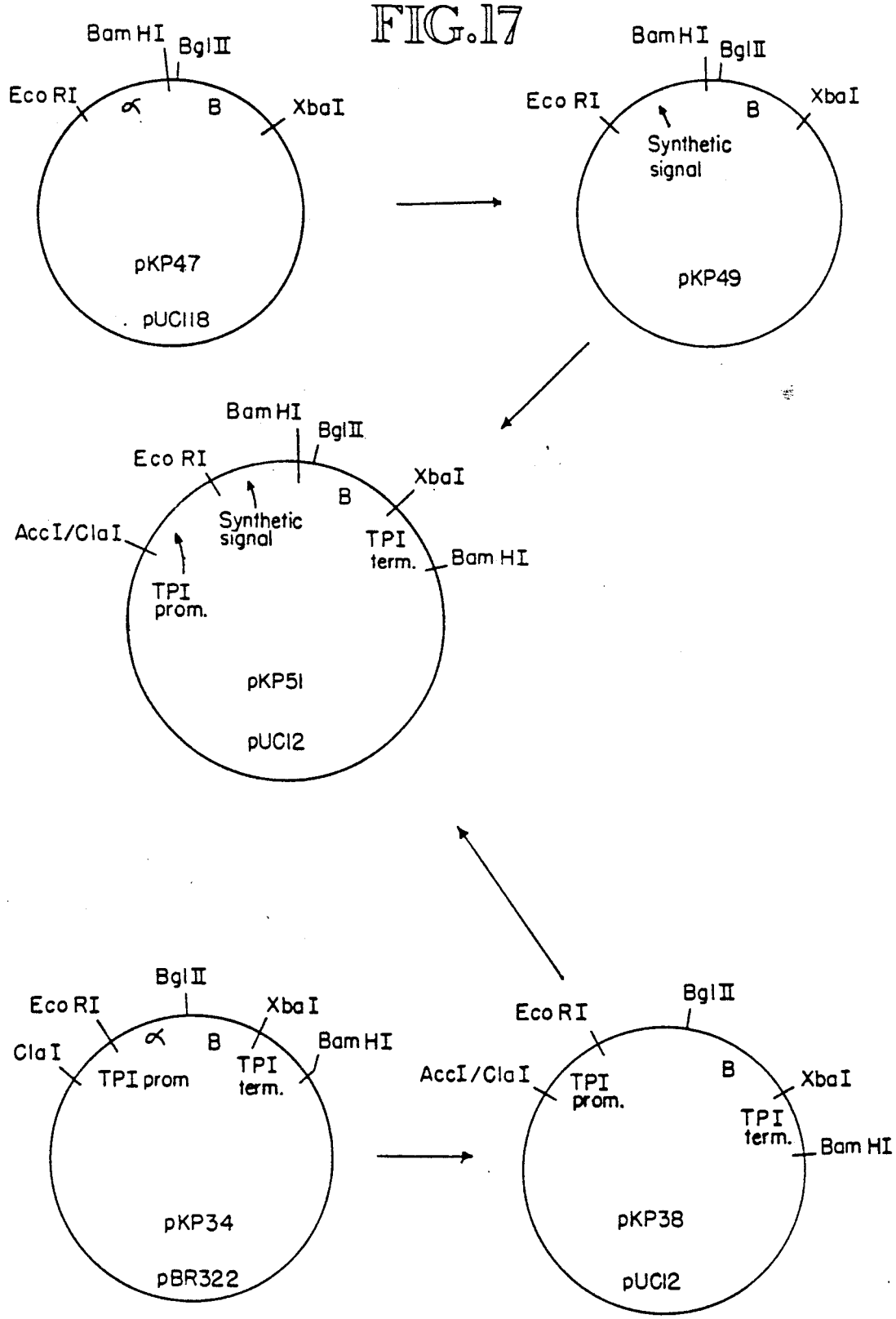
FIG. 17 illustrates the construction of plasmid pKP51.

The coding sequence for PDGF B-chain was derived from plasmid pKP51 which was constructed as shown in FIG. 17. Plasmid pKP32 was transformed into *E. coli* strain MV1193. Single-stranded template DNA was prepared and the template was mutagenized using mutagenic oligonucleotide ZC1078 (Table 3). Mutagenesis of the template with ZC1078 resulted in a Bam HI restriction site insertion at the 5' end of the PDGF B-chain coding sequence. Positive clones were identified by plaque hybridization, restriction analysis and dideoxy sequencing. A positive clone was designated pKP47.

The MFα1 signal sequence present n pKP47 was replaced by a synthetic signal sequence. Plasmid pKP47 was digested with Eco RI and Bam HI to isolate the fragment comprising the human B-chain sequence and pUC118 vector sequences. Oligonucleotides ZC1157, ZC1158, ZC1076 and ZC1077 (Table 3) were designed to encode, when annealed, an Eco RI-Bam HI adapter encoding a synthetic signal sequence. Oligonucleotides ZC1158 and ZC1076 were kinased. Oligonucleotides ZC1158 and ZC1157 were annealed and ZC1076 and ZC1077 were annealed in separate reactions. The Eco RI-Bam HI fragment from pKP47 was joined with ZC1158/ZC1157 and ZC1076/ZC1077 in a three-part ligation. The resultant plasmid, designated pKP49, comprised the synthetic signal sequence, the PDGF B-chain sequence and pUC118 vector sequences.

An expression unit comprising the TPI1 promoter, synthetic signal sequence, PDGF B-chain sequence and TPI1 terminator was constructed from plasmid pKP49 for subsequent subcloning into a yeast expression vector. Plasmid pKP34 was digested with Cla I and Bam HI to isolate the 2.3 kb fragment comprising the TPI1 promoter, MFα1 signal sequence, PDGF B-chain sequence and TPI1 terminator expression unit. Plasmid pUC12 was linearized by digestion with Hind III and Eco RI. Oligonucleotides ZC1016 and ZC1017 (Table 3) were kinased and annealed to form a polylinker adapter comprising Cla I, Hind III, Xho I, Acc I, Xba I and Bam HI restriction sites. The linear vector was joined with the kinased and annealed ZC1016/ZC1017 adapter by ligation, resulting in the loss of the pUC12 Hind III and Eco RI sites. The resultant vector, pUC12*, was linearized by digestion with Acc I and Bam HI. The 2.3 kb expression unit fragment was joined to the linearized pUC12* by ligation. The resultant plasmid was designated pKP38. Plasmid pKP38 was digested with Eco RI and Xba I to isolate the 4.3 kb fragment comprising the TPI1 promoter, TPI1 terminator and pUC12* vector sequences. Plasmid pKP49 was digested with Eco RI and Xba I to isolate the 0.8 kb fragment comprising the synthetic signal sequence and PDGF B-chain sequence. The 0.8 kb fragment was joined to the 4.3 kb fragment from pKP37 by ligation. The resultant plasmid was designated pKP51.

B. Expression Vector Construction

The PDGF B-chain sequence was then joined to a secretion signal comprising the leader and third domain coding sequences of the *S. cerevisiae* BAR1 gene. The BAR1 secretion signal was then combined with the B-chain coding sequence to construct expression vectors pSW304 and pZY76.

Plasmid pSW255, comprising the TPI1 promoter and BAR1 secretion signal, was first constructed. The third domain coding sequence of BAR1 present in plasmid pSW195 (Example 5) was fused to a synthetic adapter which encodes amino acids 81 through 85 of alpha factor, a Lys-Arg cleavage site, a 5' Eco RI adhesive end, a 3' Bgl II adhesive end and the first amino acid of the PDGF B-chain. Oligonucleotides ZC1135 and ZC1136 (Table 3) were kinased and annealed essentially as described by Maniatis et al. (ibid.). Plasmid pSW195 was digested with Hind III and Eco RI to isolate the 1.4 kb fragment comprising the TPI1 promoter and BAR1 coding sequences. The 1.4 kb fragment was joined with the ZC1135/ZC1136 adapter and pIC19R, which had been linearized by digestion with Hind III and Bgl II in a three-part ligation. The resultant plasmid was designated pSW255 (FIG. 18).

Figure 18:
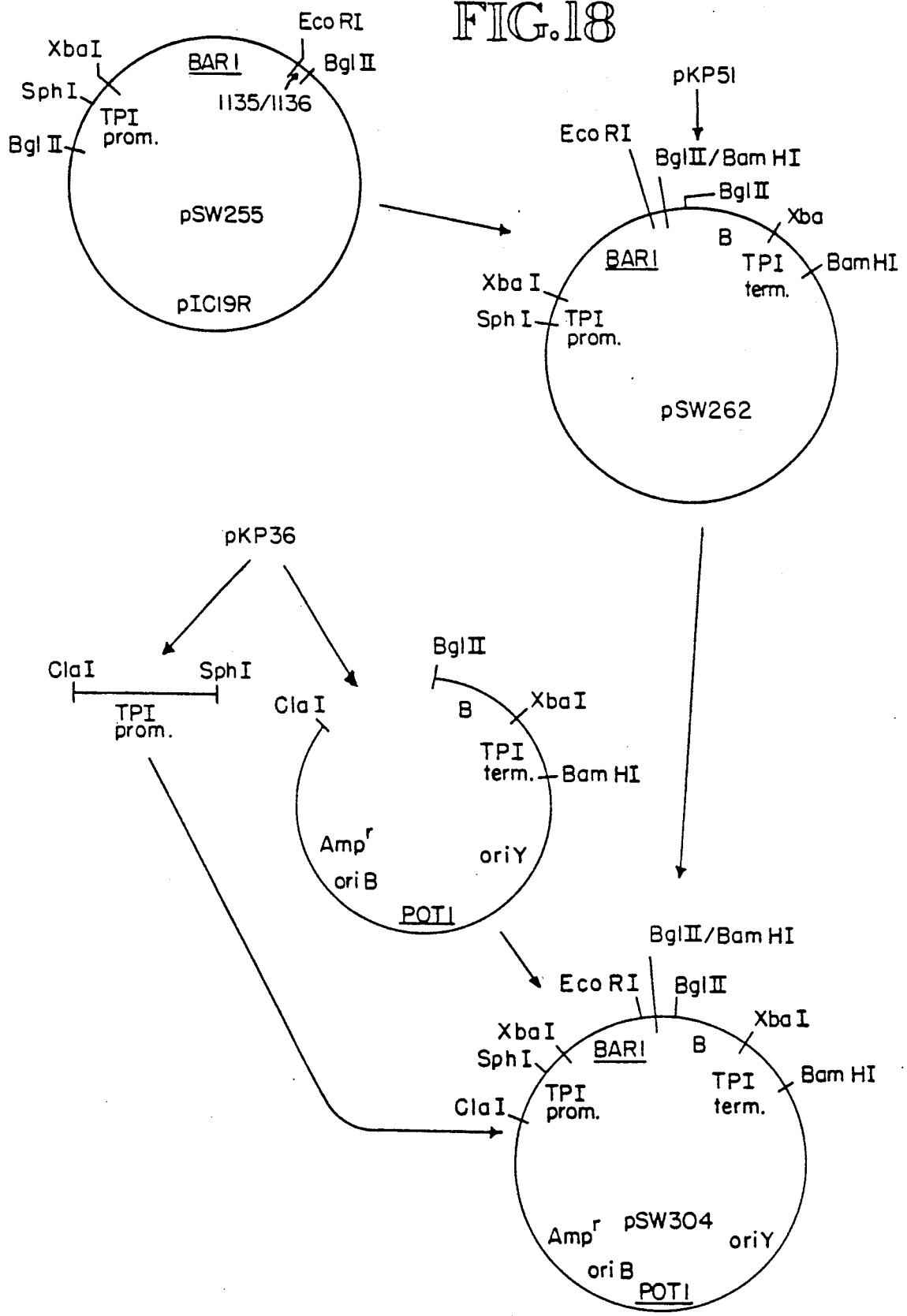
FIG. 18 illustrates the construction of expression vector pSW304.

The PDGF B-chain sequence present in plasmid pKP51 was joined with the TPI1 promoter, BAR1 signal sequence, BAR1 third domain and ZC1135/ZC1136 adapter (encoding a Lys-Arg cleavage site) to construct plasmid pSW262 (FIG. 18). Plasmid pKP51 was digested with Bam HI to isolate the 1.09 kb fragment comprising the PDGF B-chain coding sequence and the TPI1 terminator. Plasmid pSW255 was digested with Sph I and Bgl II to isolate the 0.75 kb fragment comprising the partial TPI1 promoter, BAR1 signal sequence, BAR1 third domain and the ZC1135/ZC1136 adapter. The two fragments were joined in a three-part ligation with pUC18 which had been linearized with Sph I and Bam HI. A plasmid was identified which contained the component fragments in the correct orientation and was designated pSW262.

The yeast expression vector pSW304, comprising the TPI1 promoter, BAR1 signal sequence, BAR1 third domain, PDGF B-chain and the TPI1 terminator in the vector pMPOT2, was then constructed as shown in FIG. 18. Plasmid pKP36 was digested with Cla I and Sph I to isolate the 0.76 kb 5' portion of the TPI1 promoter. Plasmid pKP36 (FIG. 16) was also digested with Cla I and Bgl II to isolate the 11 kb vector-containing fragment comprising the PDGF B-chain sequence, TPI1 terminator and pMPOT2 vector sequences. Plasmid pSW262 was digested with Sph I and Bgl II to isolate the 0.75 kb partial TPI1 promoter, BAR1 signal sequence, BAR1 third domain and ZC1135/ZC1136. The three fragments were joined in a three-part ligation and the resultant plasmid was designated pSW304.

Figure 19:
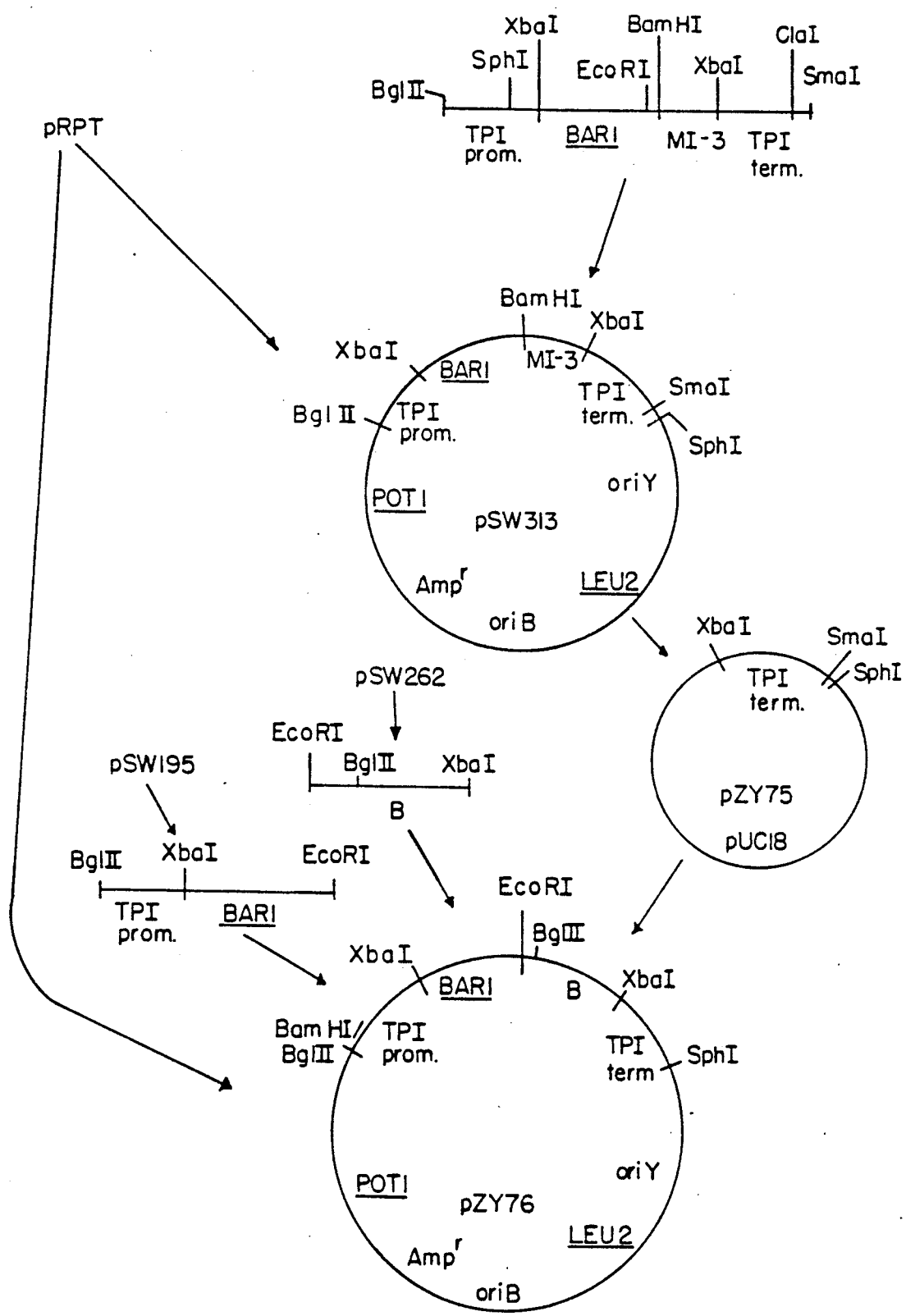
FIG. 19 illustrates the construction of expression vector pZY76.

Expression vector pZY76 (FIG. 19) was constructed by inserting a B-chain expression unit into the vector pRPOT. The pRPOT vector was derived from pCPOT (ATCC 39685) by first replacing the 750 bp Sph I-Bam HI fragment of pCPOT with a 186 bp Sph I-Bam HI fragment of pBR322. The resultant plasmid, pDPOT, was digested with Sph I and Bam HI to isolate the 10.8

TABLE 3

| Oligonucleotide | Sequence (5'→3') | | | | | | | | |
|---|---|---|---|---|---|---|---|---|---|
| ZC1016 | AAT | TTA | TCG | ATA | AGC | TTG | ACT | CGA | GAG | TCG |
|  | ACT | CTA | GAG | GAT | CCG |  |  |  |  |
| ZC1017 | AGC | TCG | GAT | CCT | CTA | GAG | TCG | ACT | CTC | GAG |
|  | TCA |  |  |  |  |  |  |  |  |
|  | AGC | TTA | TCG | ATA |  |  |  |  |  |
| ZC1076 | AGC | TTT | CTT | GTT | CTT | GTT | GGC | TGG | TTT | CGC |
|  | TGC | TAA | GAT | TTC | TCC | AGG | TGC | TTT | CG |
| ZC1077 | GAT | CCG | AAA | GCA | CCT | GGA | GAA | ATC | TTA | GCA |
|  | GCG | AAA | CCA | GCC | AAC | AAG | AAC | AAG | AA |
| ZC1078 | GAA | CCC | AAG | GAT | CCG | AGC | TCC | AAA | GAA | ACA |
| ZC1136 | AAT | TCA | TTG | GAT | AAG | A |  |  |  |  |
| ZC1135 | GAT | CTC | TTA | TCC | CAT | G |  |  |  |  |
| ZC1157 | AAT | TCT | AAA | AAT | GCT | TTT | GCA |  |  |  |
| ZC1158 | AGC | TTG | CAA | AAG | CAT | TTT | TAG |  |  |  |
| ZC1551 | GAT | CCC | CGG | GGA | GCT | CCT | CGA | GGC | ATG |  |
| ZC1552 | CCT | CGA | GGA | GCT | CCC | CGG | G |  |  |  | kb fragment. Oligonucleotides ZC1551 and ZC1552 (Table 1) were kinased and annealed to form an adapted with a Bam HI adhesive end and an Sph I adhesive end flanking Sma I, Sst I and Xho I restriction sites. The 10.8 kb pDPOT fragment was recircularized by ligation with the ZC1551/ZC1552 adapter. The resultant plasmid was termed pRPOT.

The TPI1 terminator was subcloned as follows. Plasmid pSW195 (FIG. 11) was digested with Bgl II and Sma I to isolate the 2.38 kb fragment comprising the TPI1 promoter, the BAR1 amino terminus and third domain, the MI-3 coding sequence, and the TPI1 terminator. The 2.38 kb fragment was ligated with plasmid pRPOT, which had been linearized by digestion with Sma I and Bgl II. The resulting plasmid, designated pSW313, was digested with Xba I and Sph I to isolate the 0.76 kb TPI1 terminator fragment. The 0.76 kb fragment was joined with pUC18, which had been linearized by digestion with Sph I and Xba I. The resultant plasmid was designated pZY75.

Plasmid pZY76 was then assembled. Plasmid pSW195 was digested with Bgl II and Eco RI to isolate the 1.4 kb fragment comprising the TPI1 promoter and the BAR1 amino terminus and third domain. Plasmid pSW262 (FIG. 18) was digested with Eco RI and Xba I to isolate the 0.35 kb fragment comprising the ZC1135/ZC1136 adapter and the PDGF B-chain coding sequence. Plasmid pZY75 was digested with Xba I and Sph I to isolate the 0.75 kb fragment comprising the TPI1 terminator. The three fragments were joined with pRPOT, which had been linearized by digestion with Bam HI and Sph I, in a four-part ligation. The resultant plasmid, comprising the TPI1 promoter, BAR1 amino terminus and third domain, the PDGF coding sequence, the TPI1 terminator and pRPOT vector sequences, was designated pZY76.

C. Expression of BB Homodimer

The expression of PDGF BB from yeast strains transformed with pSW304 and pZY76 was compared to expression of PDGF from control plasmids pB170m (Murray et al. U.S. Ser. No. 896,485) and pKP57 (comprising the pKP34 expression unit in pRPOT). Plasmids pSW304, pZY76, pB170m, and pKP57 were transformed into yeast strains E18 #9 (MATa leu2-3,112 his4-580 pep4-3 Δtpi1::LEU2/MATα leu2-3,112 pep4-3 Δtpi1::LEU2), XB13-5B (MATα leu2-3,112 ura3 bar1 gal2 Δtpi1::URA3 [cir°]) and ZM114 (MATa ade2-101 leu2-3,112 ura3-52 Δtpi1::URA3 vpt3 suc2-Δ9 gal2 pep4::TPI promoter-CAT [cir°]) essentially as described by Beggs (*Nature* 275:104–108, 1978).

Transformants from single colonies were inoculated into fermentation medium (Table 4) and grown for 24 hours at 30° C. After 24 hours glucose was added to the cultures to a final concentration of 2% and the cultures were grown for 24 hours at 30° C.

TABLE 4

| Fermentation Medium |
|---|
| 20 g NZ Amine Type A |
| 7 g KH$_2$PO$_4$ |
| 6 g NH$_4$SO$_4$ |
| 2 g MgSO$_4$ |

Dissolve the solids in water and bring the volume to one liter. Autoclave for 25 minutes. After autoclaving add 2 ml/l Trace Elements Solution (recipe following), 3 ml Vitamin Solution (recipe following), 2M sodium succinate, pH 5.5 to a final molarity of 0.1M and 50% glucose to a final concentration of 2%.

Trace Elements Solution 9.45 mg ZnSO$_4$
284.8 mg Fe$_2$(SO$_4$)$_3$
48 mg CuSO$_4$.5H$_2$O Dissolve the solids in distilled water and bring to a final volume of 100 ml. Filter sterilize.

Vitamin Solution 420 mg riboflavin
5.4 g pantothenic acid
6.1 g niacin
1.4 g pyrodoxin
60 mg biotin
40 mg folic acid
6.6 g inositol
1.3 g thiamine Dissolve in distilled water and bring to a final volume of one liter. Filter sterilize.

The cells were removed from the medium by centrifugation. The supernatants were subsequently filtered through 0.45 μm filters to remove any cells or cell debris. Mitogenesis assays were performed on the filtered culture supernatants as described by Raines and Ross (*Meth. Enzymology* 109:749–773, 1985). The results, expressed in ng of PDGF activity per ml of culture medium, are shown in Table 5.

TABLE 5

| Plasmid: | E18#9 | XB13-5B | ZM114 |
|---|---|---|---|
| pMPOT2 | 0 | 0 | — |
| pSW304 | 800–930 | 930–1630 | — |
| pB170m | 625–830 | 1600–2300 | — |
| pMPOT2 | 0 | 0 | 0 |
| pSW304 | 1266–2300 | 3100–3200 | 826–1125 |
| pB170m | 1000–1150 | — | — |
| pRPOT | 0 | 0 | 0 |
| pZY76 | 2066–2250 | 2300–3000 | 2250–2500 |
| pKP57 | 1500–2325 | 1600–2500 | |

PDGF analogs produced by transformed yeast cells are purified from concentrated culture supernatants by a series of chromatography and concentration steps.

Culture supernatants are concentrated using Millipore Pellican Cassettes (Millipore, Bedford, Mass.) and the concentrates are pelleted by centrifugation in a Beckman J-6B centrifuge (Beckman Instruments, Inc., Brea, Calif.) at 4200 rpm for 30 minutes to remove the turbidity. EDTA is added to a final concentration of 10 mM and the pH of the mixtures is adjusted to pH 5.5 with 5M NaOH. The concentrates are then diluted with water to a conductivity of about 10 millimhos.

The resultant concentrates are chromatographed on an S-Sepharose Fast Flow (Pharmacia, Piscataway, N.J.) column. The column is washed with 20 mM sodium phosphate, 0.1M sodium chloride, pH 7.3. The column is then eluted with 20 mM sodium phosphate, 1M sodium chloride, pH 7.3. The absorbance at 280 nm of the eluate is followed and the peak fractions are collected and pooled.

The eluates are frozen at −20° C. and then thawed. The particulate material is removed from the eluates by centrifugation. The supernatants are harvested and the pH adjusted to 3.0 with 0.87M acetic acid. The eluates are then concentrated using an Amicon YM10 filter (Amicon, Danvers, Mass.). The concentrated eluates are diluted with five volumes of 1M acetic acid to lower the sodium chloride concentration to about 0.2M.

The eluates are then chromatographed on a second S-Sepharose column. The column is washed with 1M acetic acid and the absorbance at 280 nm of the eluates is followed until it returns to baseline. The column is eluted with 1M acetic acid, 1.5M ammonium chloride, pH 4.8–5.0. The $A_{280}$ of the eluates is followed and the PDGF is harvested as the last $A_{280}$ peak. The peak fractions are pooled and concentrated using an Amicon YM10 filter.

The concentrated eluates are then applied to a Sephadex G-50 Superfine (Pharmacia, Piscataway N.J.) column using a sample volume of about 1% of the column volume. The column is run at a flow rate of 5 cm/hr in 1M ammonium acetate pH 9.0. The purest fractions, as determined by SDS-gel electrophoresis, are pooled and the pH adjusted to 4.0 with acetic acid.

Example 16: Use of BAR1 Leader to Secrete Epidermal Growth Factor and Transforming Growth Factor Alpha Coding sequences for epidermal growth factor (EGF) and transforming growth factor $\alpha$ (TGF$\alpha$) were prepared from synthetic oligonucleotides. The sequences were then used to construct expression units comprising the TPI1 promoter and terminator and the BAR1 leader and third domain sequences.

Referring to FIG. 20, the EGF coding sequence was constructed from oligonucleotides ZC1734, ZC1735, ZC1534 and ZC1535. Oligonucleotide pairs (ZC1734+ZC1735 and ZC1534+ZC1535) were separately annealed incubation at 100° C. in a water bath for five minutes, followed by a slow cooling in the water bath for 60 minutes. The annealed pairs were then combined and ligated. The assembled coding fragment was cloned into M13mp19 for confirmation of the sequence. The resultant clone was designated pZY77.

Again referring to FIG. 20, the TFG$\alpha$ sequence was constructed from oligonucleotide pairs ZC1732+ZC1733 and ZC1198+ZC1200 essentially as described above for EGF. The assembled coding sequence was cloned into M13mp19 to construct pZY78.

The EGF and TGF$\alpha$ sequences were then joined to the TPI1 terminator. Phage clones pZY77 and pZY78 were digested with Eco RI and Xba I and the respective growth factor fragments were purified. Plasmid pB170SW, comprising a Sal I-Bam HI fragment containing the 3' portion of the PDGF B-chain sequence and the TPI1 terminator cloned into pIC19R, was digested with Xba I and Bam HI and the TPI1 terminator fragment was isolated. Each of the growth factor fragments was combined with the TPI1 terminator and Eco RI, Bam HI digested pUC18 in a three-part ligation. The resulting plasmids were designated pZY80 (EGF) and pZY81 (TGF$\alpha$) (FIG. 21).

Figure 21:
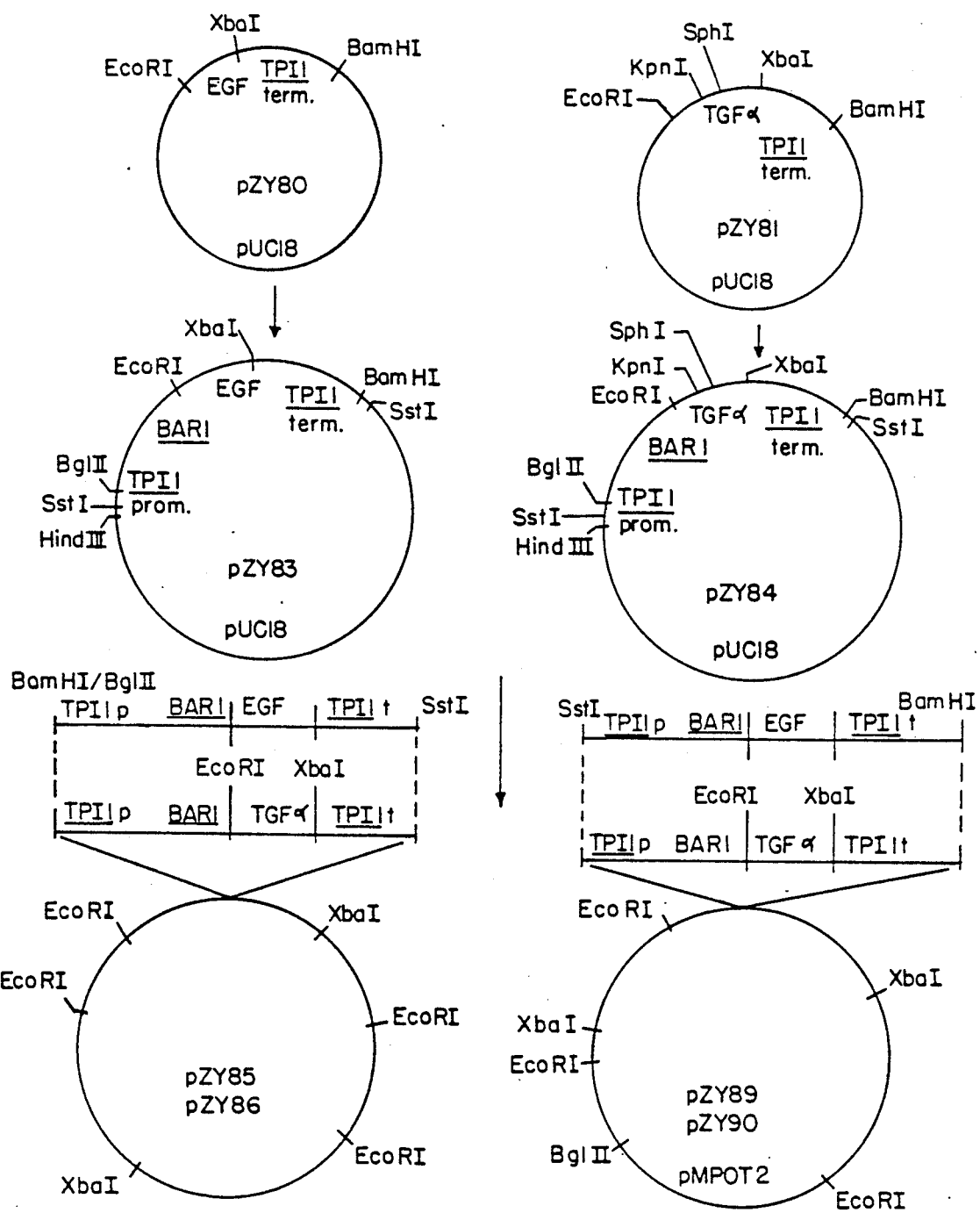
FIG. 21 illustrates the construction of expression vectors for EGF and TGFα.

The growth factor sequences were then joined to the TPI1 promoter and the BAR1 secretion signal as shown in FIG. 21. Plasmids pZY80 and pZY81 were each digested with Eco RI and Bam HI and the growth factor-terminator fragments were purified. Plasmid pSW195 (Example 5) was digested with Hind III and Eco RI and the ~1.4 kb TPI1 promoter-BAR1 fragment was isolated. The growth factor-terminator fragments were joined to the promoter-BAR1 fragment in Bam HI, Hind III digester pUC18. The resultant plasmids were designated pZY83 (EGF) and pZY84 (TFG$\alpha$).

For construction of expression vectors, pZY83 and pZY84 were each digested with Bgl II and Sst I and the expression unit fragments were isolated. The expression units were inserted into Sst I, Bam HI digested pRPOT (Example 15) to construct pZY85 (EGF) and pZY86 (TGF$\alpha$). A second set of expression vectors was constructed by inserting the Bam HI-Sst I expression units of pZY83 and pZY84 into Sst I, Bam HI digested pMPOT2 (Example 15). The resulting expression vectors were designated pZY89 (EGF) and pZY90 (TGF$\alpha$). These vectors are illustrated in FIG. 21.

For expression of EGF and TFG$\alpha$, plasmids pZY85, pZY86, pZY89 and pZY90 were transformed into S. cerevisiae strains ZM120 and ZM122 (both cir°, a/$\alpha$ diploids homozygous for leu2 ura3 tpi::LEU2 pep4-::URA3 bar1). Transformants were cultured essentially as described in Example 15. Culture supernatants were assayed for EGF and TGF$\alpha$ mitogenic activity essentially as described by Raines and Ross (Meth. Enzymology 109: 749–773, 1985), using an EGF standard.

TABLE 6

| Protein | Vector | Expression (ug/ml) in Strain | |
|---|---|---|---|
| | | ZM120 | ZM122 |
| EGF | pZY85 | 0.1–0.2 | 0.1–0.2 |
| | pZY89 | 1.3 | >8 |
| TGF$\alpha$ | pZY86 | 1.6 | >4 |
| | pZY90 | 1.1 | 1 |

Example 17: Description of Assays

A. Radioimmunoassay for MI-3 Immunoreactive Material

Radioimmunoassays were carried out on culture supernatants (prepared as described in Example 9). Samples (50 μl/well) were added to 96-well V-bottom microtiter plates (Flow Labs, McLean, Va.). Standards consisting of dilutions of porcine insulin in NaFAM (0.6 g NaCl and 5.9 g bovine serum albumin, dissolved in 100 ml 0.04M Na phosphate buffer, pH 7.4, containing 0.1% bovine serum albumin, final pH adjusted to 7.3 with NaOH) were included in each plate. To each well, 50 μl guinea pig anti-insulin antisera was added. $2.5 \times 10^5$ cpm/50 μl of $^{125}$I Fab' mouse anti-insulin was added per well. This mixture was incubated at room temperature for 2 hours. Staph A cells (Pansorbin, Sigma Chemical Co., St. Louis, Mo.) were diluted 1:10 in NaFAM, and 50 μl were added to each well, followed by a 45-minute room-temperature incubation. The plate was centrifuged for 5 minutes at 4° C. at 3,000 rpm in a Beckman TJ-6 centrifuge. The supernatants were discarded, and the wells were washed twice with 150 μl 1% bovine serum albumin (BSA) in TNEN (50mM Tris-base, 100 mM NaCl, 1 mM EDTA, 0.5% NP40, adjusted to pH 8.0). The cells were resuspended in 1% BSA in TNEN and counted on a gamma counter.

B. High-Pressure Liquid Chromatography (HPLC Assay for MI-3

TABLE 7

| HPLC Buffer Recipes |
|---|
| Buffer A: 56.8 g Na$_2$SO$_4$ |
| 1800 ml HPLC-grade H$_2$O (OmniSolv, EM Science, Cherry Hill, N.J.) |
| 5.4 ml H$_3$PO$_4$ (min 85%) |
| Adjust pH to 2.3 with ethanolamine. Adjust pH to 3.6 with 4 N NaOH. Add 156 g HPLC-grade acetonitrile (Am. |

TABLE 7-continued

HPLC Buffer Recipes

Burdick & Jackson Laboratory, Muskegon, Mich.). Adjust volume to 2 l with HPLC-grade H$_2$O. Filter through a 0.45 μm filter.
Buffer B: 780 g HPLC-grade acetonitrile
1044 g HPLC-grade H$_2$O HPLC assays were carried out on culture supernatants using a VISTA 5500 HPLC (Varian). Supernatant samples (prepared as described in Example 10) were thawed and centrifuged in a microfuge for 1 min at room temperature to remove any precipitate from the samples. MI-3 standards (obtained from Novo Industri A/S, Bagsvaerd, Denmark) of 2.0, 1.0 and 0.5 μg were made up in 0.025M formic acid. 100 μl of each sample and standard were loaded onto a C18 reverse-phase column (LiChroprep RP-18 (5 μm), E. Merck, Darmstad, FR Germany).

The column was run using an isocratic gradient comprising 60% Buffer A and 40% Buffer B (recipes listed in Table 7) at 50° C. at a flow rate of 1 ml/min with a detection level of 214 nm, 0.05 AUFS (Absorbance Units Full Scale). Each sample was run for 30 min, with the MI-3 peak emerging at 18 min. Quantitation of MI-3 material is based on comparison of the sample material with the known MI-3 standards.

C. Quantitative Fibrin Lysis Assay for uPA Activity

Appropriately grown cultures, as described in the examples, were centrifuged to pellet the cells. The supernatants were decanted and saved. The cell pellets were washed once with water and resuspended in phosphate-buffered saline (PBS, Sigma Chemical Co.) +5 mM EDTA. Glass beads (450-500 μm) are added to one-half the total volume. The mixtures were vortexed at full speed for one minute, three times, with the samples cooed on ice between vortex bursts. The liquid was removed from the tubes with a pasteur pipet and transferred to microfuge tubes. The lysates were then centrifuged in an Eppendorf microfuge (Brinkmann, Westbury, N.Y.) at top speed for 15 min at 4° C. The supernatants were carefully removed for assay.

The fibrin lysis assay is based on the method of Binder et al. (*J. Biol. Chem.* 254:1998, 1979). 150 mg Agarose B (Pharmacia) was added to 15 ml Fibrin Plate Buffer (4.36 gm Tris-base, 8.48 gm NaCl, 15 mg CaCl$_2$, 200 mg NaN$_3$ in 1 liter, pH adjusted to pH 8.4). The agarose mixture was melted and held at 55° C. To this solution was added 10 μl bovine thrombin (500 U/ml). Fibrinogen (Sigma Chemical Co.) was dissolved in Fibrin Plate Buffer, filter-sterilized, then diluted to an O.D. 280 of 5 with Fibrin Plate Buffer. 5 ml of the fibrinogen solution was added to the agarose-thrombin solution. The mixture was poured onto a Gelbond agarose support sheet (FMC Corp., Rockland, Me.) and allowed to cool. Wells were cut in the agarose and to the wells was added 10 μl or 20 μl of the sample to be tested. Results were compared to a human urokinase standard curve and adjusted to the reduced specific activity of porcine urokinase. The development of a clear halo around the well indicates the presence of biologically active porcine urokinase.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A DNA construct comprising the following operably linked elements:
   a transcriptional promoter;
   a first DNA sequence encoding a signal peptide;
   a second DNA sequence encoding at least a portion of the C-terminal domain of the BAR1 gene product capable of directing the export of heterologous proteins when used in combination with a signal peptide; and
   a third DNA sequence encoding a heterologous protein or polypeptide.

2. The DNA construct of claim 1 wherein the portion of the C-terminal domain comprises the amino acid sequence of FIG. 1, beginning with serine, number 391, and ending with serine, number 526.

3. The DNA construct of claim 1 wherein the portion of the C-terminal domain comprises the amino acid sequence of FIG. 1, beginning with alanine, number 423, and ending with serine, number 526.

4. The DNA construct of claim 1 wherein said heterologous protein or polypeptide is a protein selected from the group consisting of urokinase, insulin, platelet-derived growth factor, epidermal growth factor, transforming growth factor α and analogs thereof.

5. The DNA construct of claim 1 wherein sad transcriptional promoter is that of a gene encoding a TPI enzyme or an ADH enzyme.

6. The DNA construct of claim 1 wherein the signal peptide is the Barrier signal peptide or the yeast repressible acid phosphatase signal peptide.

7. The DNA construct of claim 1 wherein said second DNA sequence is followed in the 5' to 3' direction by said third DNA sequence.

8. The DNA construct of claim 1 where said third DNA sequence is followed in the 5' to 3' direction by said second DNA sequence.

9. The DNA construct of claim 7 or 8 wherein said second DNA sequence further comprises a DNA sequence encoding a proteolytic cleavage site operably linked to said third DNA sequence.

10. The DNA construct of claim 9 wherein said cleavage site is a dibasic cleavage site or a thrombin cleavage site.

11. The DNA construct of claim 1 wherein the second DNA sequence is mutagenized to prevent carbohydrate addition at one or both of amino acids 468 and 503 of the BAR1 gene product.

12. The DNA construct of claim 11 wherein the second DNA sequence encodes a glutamine residue at amino acid 468 of the BAR1 gene product.

13. The DNA construct of claim 11 wherein the second DNA sequence encodes a glutamine residue at amino acid 503 of the BAR1 gene product.

14. A yeast cell transformed with a DNA construct comprising the following operably linked elements:
   a transcriptional promoter;
   a first DNA sequence encoding a signal peptide;
   a second DNA sequence encoding at least a portion of the C-terminal domain of the BAR1 gene product capable of directing the export of heterologous proteins when used in combination with a signal peptide; and
   a third DNA sequence encoding a heterologous protein or polypeptide.

15. The yeast cell of claim 14 wherein the portion of the C-terminal domain comprises the amino acid sequence of FIG. 1, beginning with serine, number 391, and ending with serine, number 526.

16. The yeast cell of claim 14 wherein the portion of the C-terminal domain comprises the amino acid sequence of FIG. 1, beginning with alanine, number 423, and ending with serine, number 526.

17. The yeast cell of claim 14 wherein the signal peptide is the Barrier signal peptide or the yeast repressible acid phosphatase signal peptide.

18. The yeast cell of claim 14 wherein said second DNA sequence is followed in the 5' to 3' direction by said third DNA sequence.

19. THe yeast cell of claim 14 wherein said third DNA sequence is followed in the 5' to 3' direction by said second DNA sequence.

20. The yeast cell of claims 18 or 19 wherein said second DNA construct further comprises a DNA sequence encoding a proteolytic cleavage site operably linked to said third DNA sequence.

21. The yeast cell of claim 20 wherein said cleavage site is a dibasic cleavage site or a thrombin cleavage site.

22. The yeast cell of claim 14 wherein the second DNA sequence is mutagenized to prevent carbohydrate addition at one or both of amino acids 468 and 503 of the BAR1 gene product.

23. The yeast cell of claim 22 wherein the second DNA sequence encodes a glutamine residue at amino acids 468 of the BAR1 gene product.

24. The yeast cell of claim 22 wherein the second DNA sequence encodes a glutamine residue at amino acid 503 of the BAR1 gene product.

25. A mammalian cell transformed with a DNA construct comprising the following operably linked elements:
a transcriptional promoter;
a first DNA sequence encoding a signal peptide;
a second DNA sequence encoding at least a portion of the C-terminal domain of the BAR1 gene product capable of directing the export of heterologous proteins when used in combination with a signal peptide; and
a third DNA sequence encoding a heterologous protein or polypeptide.

26. The mammalian cell of claim 25 wherein the portion of the C-terminal domain comprises the amino acid sequence of FIG. 1, beginning with serine, number 391, and ending with serine, number 526.

27. The mammalian cell of claim 25 wherein the portion of the C-terminal domain comprises the amino acid sequence of FIG. 1, beginning with alanine, number 423, and ending with serine, number 526.

28. The mammalian cell of claim 25 wherein said second DNA sequence is followed in the 5' to 3' direction by said third DNA sequence.

29. The mammalian cell of claim 25 wherein said third DNA sequence is followed in the 5' to 3' direction by said second DNA sequence.

30. The mammalian cell of claim 28 or 29 wherein said second DNA sequence further comprises a DNA sequence encoding a proteolytic cleavage site operably linked to said third DNA sequence.

31. The mammalian cell of claim 30 wherein said cleavage site is a dibasic cleavage site or a thrombin cleavage site.

32. The mammalian cell of claim 25 wherein the second DNA sequence is mutagenized to prevent carbohydrate addition at one or both of amino acids 468 and 503 of the BAR1 gene product.

33. The mammalian cell of claim 32 wherein the second DNA sequence encodes a glutamine residue at amino acid 468 of the BAR1 gene product.

34. The mammalian cell of claim 32 wherein the second DNA sequence encodes a glutamine residue at amino acid 503 of the BAR1 gene product.

35. A method of producing a secreted protein of interest, comprising:
growing a host cell containing a DNA construct comprising the following operably linked elements:
a transcriptional promoter;
a first DNA sequence encoding a signal peptide;
a second DNA sequence encoding at least a portion of the C-terminal domain of the BAR1 gene product capable of directing the export of heterologous proteins when used in combination with a signal peptide; and
a third DNA sequence encoding a heterologous protein or polypeptide in an appropriate medium; and
isolating the protein or polypeptide product from said medium.

36. The method of claim 35, including, after the step of isolating, purifying said protein product.

37. The method of claim 35 wherein said host cell is a yeast cell or a mammalian cell.

38. The method of claim 35 wherein the portion of the C-terminal domain comprises the amino acid sequence of FIG. 1, beginning with serine, number 391, and ending with serine, number 526.

39. The method of claim 35 wherein the portion of the C-terminal domain comprises the amino acid sequence of FIG. 1, beginning with alanine, number 423, and ending with serine, number 526.

40. The method of claim 35 wherein the second DNA sequence is mutagenized to prevent carbohydrate addition at one or both of amino acids 468 and 503 of the BAR1 gene product.

41. The method of claim 40 wherein the second DNA sequence encodes a glutamine residue at amino acid 468 of the BAR1 gene product.

42. The method of claim 40 wherein the second DNA sequence encodes a glutamine residue at amino acid 503 of the BAR1 gene product.

43. The DNA construct of claim 1 wherein said second DNA sequence encodes a portion of the C-terminal domain consisting essentially of between 103 and 136 amino acids and comprising the amino acid sequence of FIG. 1 from alanine, number 423 through serine, number 526 of the BAR1 gene product.

44. The yeast cell of claim 14 wherein said second DNA sequence encodes a portion of the C-terminal domain consisting essentially of between 103 and 136 amino acids and comprising the amino acid sequence of FIG. 1 from alanine, number 423 through serine, number 526 of the BAR1 gene product.

45. The mammalian cell of claim 25 wherein said second DNA sequence encodes a portion of the C-terminal domain consisting essentially of between 103 and 136 amino acids and comprising the amino acid sequence of FIG. 1 from alanine, number 423 through serine, number 526 of the BAR1 gene product.

46. The method of claim 35 wherein said second DNA sequence encodes a portion of the C-terminal domain consisting essentially of between 103 and 136 amino acids and comprising the amino acid sequence of FIG. 1 from alanine, number 423 through serine, number 526 of the BAR1 gene product.

* * * * *